United States Patent

Bomhard et al.

Patent Number: 4,737,495
Date of Patent: Apr. 12, 1988

[54] (2H)-3-BENZAZEPIN-2-ONES, THEIR PHARMACEUTICAL COMPOSITIONS AND THEIR PHARMACEUTICAL USES

[75] Inventors: Andreas Bomhard; Manfred Psiorz, both of Biberach; Joachim Heider, Warthausen; Norbert Hauel, Biberach; Klaus Noll, Warthausen; Berthold Narr, Biberach, all of Fed. Rep. of Germany; Walter Kobinger; Christian Lillie, both of Vienna, Austria

[73] Assignee: Dr. Karl Tomae, GmbH, Biberach and der Riss, Fed. Rep. of Germany

[21] Appl. No.: 868,986

[22] Filed: May 30, 1986

[30] Foreign Application Priority Data

Jun. 1, 1985 [DE] Fed. Rep. of Germany ....... 3519735
Jun. 24, 1985 [DE] Fed. Rep. of Germany ....... 3522552

[51] Int. Cl.$^4$ ............... C07D 403/12; C07D 405/12; C07D 409/12; C07D 417/12; C07D 233/16; C07D 401/12; C07D 413/12; A61K 31/55; A61K 31/47; A61K 31/445
[52] U.S. Cl. ............................ 514/213; 514/215; 540/521; 540/523
[58] Field of Search ............... 540/521, 523; 514/215, 514/213

[56] References Cited

U.S. PATENT DOCUMENTS 4,490,369 12/1984 Reiffen et al. .................. 540/521
4,616,011 10/1986 Reiffen et al. .................. 540/521

Primary Examiner—Robert T. Bond
Attorney, Agent, or Firm—David E. Frankhouser; Mary-Ellen M. Timbers

[57] ABSTRACT

The invention relates to new heteroaromatic amine derivatives of formula

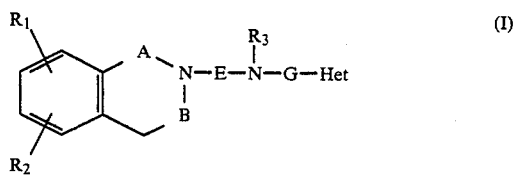

wherein
A represents a —CH$_2$—CH$_2$—, —CH=CH— or —CH$_2$—CO—
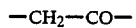
group and B represents a methylene, carbonyl or thiocarbonyl group or
A represents a —CO—CO or

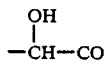

group and B represents a methylene group, in which the carbon atom marked x is linked to the phenyl nucleus,
E represents a straight-chained alkylene group optionally substituted by an alkyl group,
G represents a straight-chained alkylene group optionally substituted by an alkyl group,
R$_1$ represents a hydrogen, fluorine, chlorine or bromine atom, a trifluoromethyl, nitro, amino, alkylamino, dialkylamino, alkyl, alkylmercapto, hydroxy, alkoxy or phenylalkoxy group,
R$_2$ represents a hydrogen, chlorine or bromine atom or a hydroxy, alkoxy, phenylalkoxy or alkyl group or
R$_1$ and R$_2$ together represent an alkylenedioxy group,
R$_3$ represents a hydrogen atom, an alkenyl group, an alkyl or phenylalkyl group, and
Het represents a 5- or 6-membered heteroaromtic ring bonded via a carbon or nitrogen atom, which contains an oxygen, sulphur or nitrogen atom, two nitrogen atoms or a nitrogen atom and an oxygen or sulphur atom, and onto which additionally a phenyl ring can be condensed, in which case the bond can also be via the phenyl nucleus, or an imidazo[1,2-a]pyridyl group wherein the carbon structure of the above-mentioned groups can be substituted by a methylenedioxy or ethylenedioxy group or can be mono- or disubstituted by a halogen atom or an alkyl, hydroxy, alkoxy, phenylalkoxy, phenyl, dimethoxyphenyl, nitro, amino, acetylamino, carbamoylamino, N-alkylcarbamoylamino, hydroxymethyl, mercapto, alkylmercapto, alkylsulphinyl, alkylsulphonyl, alkylsulphonyloxy, alkylsulphonylamino, alkoxycarbonylmethoxy, carboxymethoxy or alkoxymethyl group, and at the same time any imino group present in the above-mentioned heteroaromatic groups can be substituted by an alkyl, phenylalkyl or phenyl group, the N-oxides and the acid addition salts thereof with inorganic or organic acids, which have valuable pharmacological properties, particularly the effect of lowering heart rate and oxygen requirement of the heart. They can be used to treat sinus tachycardia or ischaemic heart disease.

11 Claims, No Drawings

(2H)-3-BENZAZEPIN-2-ONES, THEIR PHARMACEUTICAL COMPOSITIONS AND THEIR PHARMACEUTICAL USES

The present invention relates to new heteroaromatic amine derivatives of formula I

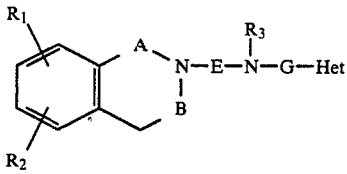

the N-oxides thereof, the acid addition salts thereof, particularly the non-toxic, pharmaceutically acceptable acid addition salts with inorganic or organic acids, processes for preparing them and pharmaceutical compositions containing these compounds and methods of using them to prevent or treat disease.

The new compounds have valuable pharmacological properties, particularly a long-lasting lowering effect on heart rate and the effect of reducing the $O_2$ requirements of the heart.

In formula I above:
A represents a $-CH_2-CH_2-$, $-CH=CH-$ or

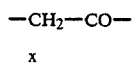

group and
B represents a methylene, carbonyl or thiocarbonyl group or
A represents a $-CO-CO-$ or

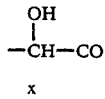

group and B represents a methylene group,
wherein the carbon atom marked x is linked to the phenyl nucleus,
E represents a straight-chained alkylene group having 2 to 4 carbon atoms optionally substituted by an alkyl group having 1 to 3 carbon atoms,
G represents a straight-chained alkylene group having 1 to 5 carbon atoms optionally substituted by an alkyl group having 1 to 3 carbon atoms,
$R_1$ represents a hydrogen, fluorine, chlorine or bromine atom, a trifluoromethyl, nitro, amino, alkylamino, dialkylamino, alkyl, alkylmercapto, hydroxy, alkoxy or phenylalkoxy group in which each alkyl part can contain from 1 to 3 carbon atoms,
$R_2$ represents a hydrogen, chlorine or bromine atom or a hydroxy, alkoxy, phenylalkyl or alkyl group in which each alkyl part can contain from 1 to 3 carbon atoms, or
$R_1$ and $R_2$ together represent an alkylenedioxy group having 1 or 2 carbon atoms,
$R_3$ represents a hydrogen atom, an alkenyl group having 3 to 5 carbon atoms, or an alkyl or phenylalkyl group in which the alkyl part can contain 1 to 3 carbon atoms, and
Het represents a 5- or 6-membered heteroaromatic ring bonded via a carbon or nitrogen atom, which contains an oxygen, sulfur or nitrogen atom, two nitrogen atoms or a nitrogen atom and an oxygen or sulfur atom, and onto which a phenyl ring can additionally be condensed, in which case the bond can also be via the phenyl nucleus, or an imidazo[1,2-a]pyridyl group wherein the carbon structure of the above-mentioned groups can be substituted by a methylenedioxy or ethylenedioxy group or can be mono- or disubstituted by a halogen atom or an alkyl, hydroxy, alkoxy, phenylalkoxy, phenyl, dimethoxyphenyl, nitro, amino, acetylamino, carbamoylamino, N-alkyl-carbamoylamino, hydroxymethyl, mercapto, alkylmercapto, alkylsulphinyl, alkylsulphonyl, alkylsulphonyloxy, alkylsulphonylamino, alkoxycarbonylmethoxy, carboxymethoxy or alkoxymethyl group, and at the same time any imino group present in the above-mentioned heteroaromatic groups can be substituted by an alkyl, phenylalkyl or phenyl group, in which the above-mentioned alkyl parts can each contain from 1 to 3 carbon atoms.

As examples of definitions of the groups given hereinbefore:

$R_1$ can represent a hydrogen, fluorine, chlorine or bromine atom or a methyl, ethyl, n-propyl, isopropyl, trifluoromethyl, hydroxy, methoxy, ethoxy, n-propoxy, isopropoxy, methylthio, ethylthio, isopropylthio, nitro, amino, methylamino, ethylamino, n-propylamino, isopropylamino, dimethylamino, diethylamino, di-n-propylamino, diisopropylamino, methylethylamino, methyl-n-propylamino, methylisopropylamino, ethyl-n-propylamino, benzyloxy, 1-phenylethoxy, 1-phenylpropoxy, 2-phenylethoxy or 3-phenylpropoxy group, $R_2$ can represent a hydrogen, chlorine or bromine atom or a methyl, ethyl, n-propyl, isopropyl, hydroxy, methoxy, ethoxy, n-propoxy, isopropoxy, benzyloxy, 1-phenylethoxy, 2-phenylethoxy, 2-phenylpropoxy or 3-phenylpropoxy group or together with $R_1$ it can represent a methylenedioxy or ethylenedioxy group, $R_3$ can represent a hydrogen atom or a methyl, ethyl, n-propyl, isopropyl, benzyl, 1-phenylethyl, 2-phenylethyl, 1-phenylpropyl, 1-methyl-1-phenylethyl, 3-phenylpropyl, allyl, n-buten-2-yl or n-penten-2-yl group and E can represent an ethylene, n-propylene, n-butylene, 1-methyl-ethylene, 2-ethyl-ethylene, 1-propylethylene, 1-methyl-n-propylene, 2-methyl-n-propylene, 1-ethyl-n-propylene, 3-ethyl-n-propylene, 2-propyl-n-propylene or 2-methyl-n-butylene group, G can represent a methylene, ethylidene, n-propylidene, n-butylidene, 2-methyl-propylidene, ethylene, 1-methyl-ethylene, 2-ethyl-ethylene, 1-propyl-ethylene, 2-methyl-ethylene, n-propylene, n-butylene, n-pentylene, 1-methyl-n-propylene, 3-methyl-n-propylene, 1-methyl-n-butylene, 1-methyl-n-pentylene, 1-ethyl-n-propylene, 2-ethyl-n-propylene or 1-ethyl-n-butylene group and Het can represent a pyrrolyl-2-, pyrrolyl-3-, N-methyl-pyrrolyl-2-, N-methyl-pyrroyl-3-, 1,2-dimethyl-pyrrolyl-3-, 2,5-dimethyl-pyrrolyl-3-, furyl-2-, furyl-3-, 5-methyl-furyl-2-, 2-methyl-furyl-3-, 5-nitro-furyl-2-, 5-methoxymethyl-furyl-2-, benzo[b]furyl-2-, benzo[b]furyl-3-, 7-methyl-benzo[b]furyl-3-, 2-methoxy-benzo[b]furyl-3-, 3-methoxy-benzo[b]furyl-2-, 4-methoxy-benzo[b]furyl-3-, 5-methoxy-benzo[b]furyl-3-, 6-methoxy-benzo[b]furyl-3-, 7-methoxy-benzo[b]furyl-3-, 5-methoxy-3-phenyl-benzo[b]furyl-2-, 3- methyl-5-methoxy-benzo[b]furyl-2-, thienyl-2-, thienyl-3-, 5-methyl-thienyl-2-, 2-methyl-thienyl-3-, 3-methyl-thienyl-2-, 2,5-dimethyl-thienyl-3-, 4,5,6,7-tetrahydro-benzo[b]thienyl-3-, 4,5,6,7-tetrahydro-benzo[b]thienyl-2-, 5-chloro-thienyl-2-, 5-bromo-thienyl-2-, 5-phenyl-thienyl-2-, 2-phenyl-thienyl-3-, benzo[b]thienyl-2-, benzo[b]thienyl-3-, 2,5-dimethyl-benzo[b]thienyl-3-, 5-methyl-benzo[b]thienyl-3-, 6-methyl-benzo[b]thienyl-3-, 5-chloro-benzo[b]-thienyl-2-, 5-bromo-benzo[b]thienyl-3-, 6-hydroxy-benzo[b]thienyl-3-, 7-hydroxy-benzo[b]thienyl-3-, 5-hydroxy-benzo[b]thienyl-2-, 6-hydroxy-benzo[b]-thienyl-2-, 7-hydroxy-benzo[b]thienyl-2-, 3-methoxy-benzo[b]thienyl-2-, 4-methoxy-benzo[b]thienyl-2-, 5-methoxy-benzo[b]thienyl-2-, 6-methoxy-benzo[b]thienyl-2-, 7-methoxy-benzo[b]thienyl-2-, 2-methoxy-benzo[b]thienyl-3-, benzo[b]thienyl-4-, benzo[b]thienyl-5-, benzo[b]thienyl-6-, benzo[b]thienyl-7-, 4-methoxy-benzo[b]thienyl-3-, 5-methoxy-benzo[b]thienyl -3-, 6-methoxy-benzo[b]thienyl-3-, 7-methoxy-benzo[b]thienyl-3-,5,6-dimethoxy-benzo[b]thienyl-3-, 5,6-methylenedioxy-benzo[b]thienyl-3-, 6-ethoxy-benzo[b]thienyl-3-, 6-propoxy-benzo[b]thienyl-3-, 6-isopropoxybenzo[b]thienyl-3-, 6-mercapto-benzo[b]thienyl-3-, 6-methylmercapto-benzo[b]thienyl-3-, 6-methylsulfinyl-benzo[b]thienyl-3-, 6-methyl-sulfonyl-benzo[b]thienyl-3-, 6-methylsulfonyloxy-benzo[b]thienyl-3-, 6-methoxycabonylmethoxy-benzo[b]thienyl-3-, 6-ethoxycarbonylmethoxy-benzo[b]thienyl-3-, 6-carboxymethoxy-benzo[b]thienyl-3-, 6-amino-benzo[b]thienyl-3-, 6-methylamino-benzo[b]thienyl-3-, 6-dimethylamino-benzo-[b]thienyl-3-, 6-diethylaminobenzo[b]thienyl-3-, 6-acetamino-benzo[b]thienyl-3-, 6-methyl-sulfonylamino-benzo[b]thienyl-3-, pyrazolyl-1-, pyrazolyl-3-, 3,5-dimethyl-pyrazolyl-1-, 1,5-dimethyl-pyrazolyl-3-, imidazolyl-1-, imidazolyl-2-, imidazolyl-4(5), 1-methyl-imidazolyl-4-, 1-benzyl-imidazolyl-4-, 5-nitro-2-methyl-imidazolyl-1-, 2-(3,4-dimethoxyphenyl)-imidazolyl-4(5)-, benzo[d]imadazolyl-1,2benzyl-benzo[d]imadazolyl-1, benzo[d]imidazolyl-2-, imidazo[1,2-a]pyridyl-3-, oxazolyl-4-, oxazolyl-5-, isoxazolyl-3-, 3-methyl-isoxazolyl-5-, 5-methyl-isoxazolyl-3-, 3,5-dimethyl-isoxazolyl-4-, 4-methyl-thiazolyl-5-, benzo[d]oxazolyl-2-, benzo[d]isoxazolyl-3-, benzo[d]thiazolyl-2-, 5-ethoxy-benzo[d]thiazolyl-2-, benzo[d]isothiazolyl-3-, benzo[d]pyrazolyl-1-, benzo[d]pyrazolyl-3-, pyridyl-2-, pyridyl-3, pyridyl-4-, pyridyl-3-N-oxide-, 4-nitro-pyridyl-2-, 4-amino-pyridyl-2-, 4-acetylamino-pyridyl-2,4-carbamoylamino-pyridyl-2-, 4-N-methyl-carbamoylamino-pyridyl-2-, 2-chloro-pyridyl-3-, 2-chloro-pyridyl-4-, 6-chloro-pyridyl-2-, 6-hydroxymethylpyridyl-2-, quinolyl-2-, isoquinolyl-1-, 2-methyl-quinolyl-4-, 7-methyl-quinolyl-2-, 4-chloro-quinolyl-2-, 6,7-dimethoxy-quinolyl-4-, 6,7-dimethoxy-isoquinolyl-4- or 6,7-dimethoxy-isoquinolyl-4-N-oxide group.

By way of example the following compounds can be mentioned, which fall within the scope of protection of the present invention:

1-(7,8-Dimethoxy-1,3,4,5-tetrahydro-2H-3-benzazepin-2-on-3-yl)-3-[N-methyl-N-(2-(6-methoxy-benzo[b]-thienyl-3)-ethyl)-amino]propane 1-(7,8-Dimethoxy-1,3,4,5-tetrahydro-2H-3-benzazepin-2-on-3-yl)-3-[N-methyl-N-(4-(imidazolyl-1)-butyl)-amino]propane 1-(7,8-Dimethoxy-1,3,4,5-tetrahydro-2H-3-benzazepin-2,4-dion-3-yl)-3-[N-methyl-N-(2-pyridyl-4)-ethyl)-amino]propane 1-(7,8-Dimethoxy-1,3,4,5-tetrahydro-2H-3-benzazepin-2-thion-3-yl)-3-[N-methyl-N-(3-(furyl-2)-propyl)-amino]propane 1-(7,8-Dimethoxy-2,3-dihydro-1H-3-benzazepin-3-yl)-3-[N-methyl-N-(2-(furyl-2)-ethyl)-amino]propane 1-(7,8-Dimethoxy-1,3,4,5-tetrahydro-2H-3-benzazepin-2-on-3-yl)-3-[N-methyl-N-(3-(thienyl-2)-propyl)-amino]propane 1-(7,8-Dimethoxy-1,3,4,5-tetrahydro-2H-3-benzazepin-2-on-3-yl)-3-[N-methyl-N-(2-(furyl-2)-ethyl)-amino]propane 1-(7,8-Dimethoxy-1,3,4,5-tetrahydro-2H-3-benzazepin-2-on-3-yl)-3-[N-methyl-N-(3-(furyl-2)-propyl)-amino]propane 1-(7,8-Dimethoxy-1,3,4,5-tetrahydro-2H-3-benzazepin-2-on-3-yl)-3-[N-methyl-N-(2-(thienyl-2)-ethyl)-amino]propane 1-(7,8-Dimethoxy-1,3,4,5-tetrahydro-2H-3-benzazepin-2-on-3-yl)-3-[N-methyl-N-(2-thienyl-3)-ethyl)-amino]propane 1-(7,8-Dimethoxy-1,3,4,5-tetrahydro-2H-3-benzazepin-2-on-3-yl)-3-[N-methyl-N-(2-(imidazolyl-4(5)-ethyl)-amino]propane 1-(7,8-Dimethoxy-1,3,4,5-tetrahydro-2H-3-benzazepin-2-on-3-yl)-3-[N-methyl-N-(2-(5,6-dimethoxy-benzo[b]thienyl-3)-ethyl)-amino]propane 1-(7,8-Dimethoxy-1,3,4,5-tetrahydro-2H-3-benzazepin-2-on-3-yl)-3-[N-methyl-N-(2-(imidazo[1,2-a]pyridyl-3)-ethyl)-amino]-propane 1-(7,8-Dimethoxy-1,3,4,5-tetrahydro-2H-3-benzazepin-2-on-3-yl)-3-[N-methyl-N-(2-(benzo[b]thienyl-3)-ethyl)-amino]propane 1-(7,8-Dimethoxy-1,3,4,5-tetrahydro-2H-3-benzazepin-2-on-3-yl)-3-[N-methyl-N-(4-(thienyl-2)-butyl)-amino]propane 1-(7,8-Dimethoxy-1,3,4,5-tetrahydro-2H-3-benzazepin-2-on-3-yl)-3-[N-methyl-N-(2-(imidazolyl-1)-ethyl)-amino]propane 1-(7,8-Dimethoxy-1,3,4,5-tetrahydro-2H-3-benzazepin-2-on-3-yl)-3-[N-methyl-N-(2-(1-methyl-imidazolyl-4)-ethyl)-amino]propane 1-(7,8-Dimethoxy-1,3,4,5-tetrahydro-2H-3-benzazepin-2-on-3-yl)-3-[N-methyl-N-(2-(benzo[b]thienyl-3)-1-methyl-ethyl)-amino]propane 1-(7,8-Dimethoxy-1,3-dihydro-2H-3-benzazepin-2-on-3-yl)-3-[N-methyl-N-(2-(furyl-2)-ethyl)-amino]propane 1-(7,8-Dimethoxy-1,3,4,5-tetrahydro-2H-3-benzazepin-2-on-3-yl)-3-[N-methyl-N-(2-(1H-benzo[d]imidazolyl-1)-ethyl)-amino]propane 1-(7,8-Dimethoxy-1,3,4,5-tetrahydro-2H-3-benzazepin-2-on-3-yl)-3-[N-methyl-N-(2-(2-benzyl-1H-benzo[d]imidazol yl-1)-ethyl)-amino]propane 1-(7,8-Dimethoxy-1,3,4,5-tetrahydro-2H-3-benzazepin-2-on-3-yl)-3-[N-methyl-N-(2-(4-methyl-thiazolyl-5)-ethyl)amino]propane 1-(7,8-Dimethoxy-1,3,4,5-tetrahydro-2H-3-benzazepin-2-on-3-yl)-3-[N-methyl-N-(2-(1-methyl-pyrrolyl-2)-ethyl)-amino]propane 1-(7,8-Dimethoxy-1,3,4,5-tetrahydro-2H-3-benzazepin-2-on-3-yl)-3-[N-methyl-N-(picolyl-2)-amino]propane 1-(7,8-Dimethoxy-1,3,4,5-tetrahydro-2H-3-benzazepin-2-on-3-yl)-3-[N-methyl-N-(picolyl-3)-amino]propane 1-(7,8-Dimethoxy-1,3,4,5-tetrahydro-2H-3-benzazepin-2-on-3-yl)-3-[N-methyl-N-(2-(pyridyl-4)-ethyl)-amino]propane 1-(7,8-Dimethoxy-1,3,4,5-tetrahydro-2H-3-benzazepin-2-on-3-yl)-3-[N-methyl-N-(2-(pyridyl-2)-ethyl)-amino]propane 1-(7,8-Dimethoxy-1,3,4,5-tetrahydro-2H-3-benzazepin-2-on-3-yl)-3-[N-methyl-N-(2-(6,7-dimethoxy-isoquinolyl-4)-ethyl)-amino]propane 1-(7,8-Dimethoxy-1,3,4,5-tetrahydro-2H-3-benzazepin-2-on-3-yl)-3-[N-methyl-N-(2-pyridyl-3)-ethyl)-amino]propane 1-(7,8-Dimethoxy-1,2,4,5-tetrahydro-3H-3-benzazepin-3-yl)-3-[N-methyl-N-(2-(pyridyl-4)-ethyl)-amino]propane 1-(7,8-Dimethoxy-1,3,4,5-tetrahydro-2H-3-benzazepin-2-on-3-yl)-3-[N-methyl-N-(2-pyridyl-4)-ethyl)-amino]propane 1-(7,8-Dimethoxy-1,3,4,5-tetrahydro-2H-3-benzazepin-2-on-3-yl)-3-[N-methyl-N-(2-(benzo[b]furyl-3)-ethyl)-amino]propane 1-(7,8-Dimethoxy-1,3-dihydro-2H-3-benzazepin-2-on-3-yl)-3-[N-methyl-N-(2-(benzo[b]thienyl-3)-ethyl)-amino]propane 1-(7,8-Dimethoxy-1,3,4,5-tetrahydro-2H-3-benzazepin-2-on-3-yl)-3-[N-methyl-N-(3-(benzo[b]thienyl-3)-propyl)-amino]propane 1-(7,8-Dimethoxy-1,3,4,5-tetrahydro-2H-3-benzazepin-2-on-3-yl)-3-[N-methyl-N-((benzo[b]thienyl-3)-methyl)-amino]propane 1-(7,8-Dimethoxy-1,3,4,5-tetrahydro-2H-3-benzazepin-2-on-3-yl)-3-[N-methyl-N-(2-(5-methyl-benzo[b]thienyl-3)-ethyl)-amino]propane 1-(7,8-Dimethoxy-1,3,4,5-tetrahydro-2H-3-benzazepin-2-on-3-yl)-3-[N-methyl-N-(2-(6-methoxy-benzo[b]furyl-3)-ethyl)-amino]propane 1-(7,8-Dimethoxy-1,3,4,5-tetrahydro-2H-3-benzazepin-2-on-3-yl)-3-[N-methyl-N-(2-(4-methoxy-benzo[b]thienyl-3)-ethyl)-amino]propane 1-(7,8-Dimethoxy-1,3,4,5-tetrahydro-2H-3-benzazepin-2-on-3-yl)-3-[N-methyl-N-(2-(5-bromo-benzo[b]thienyl-3)-ethyl)-amino]-propane 1-(7,8-Dimethoxy-1,3,4,5-tetrahydro-2H-3-benzazepin-2-on-3-yl)-3-[N-methyl-N-(2-benzo[b]furyl-2)-ethyl)-amino]propane 1-(7,8-Dimethoxy-1,3,4,5-tetrahydro-2H-3-benzazepin-2-on-3-yl)-3-[N-methyl-N-(2-(2,5-dimethyl-thienyl-3)-ethyl)-amino]propane 1-(7,8-Dimethoxy-1,3,4,5-tetrahydro-2H-3-benzazepin-2-on-3-yl)-3-[N-methyl-N-(3-pyridyl-3-N-oxide)-propyl)-amino]propane 1-(7,8-Dimethoxy-1,3,4,5-tetrahydro-2H-3-benzazepin-1,2-dion-3-yl)-3-[N-methyl-N-(2-(pyridyl-4)-ethyl)-amino]propane 1-(7,8-Dimethoxy-1,3,4,5-tetrahydro-2H-3-benzazepin-2-on-3-yl)-3-[N-methyl-N-(2-(pyridyl-3-N-oxide)-ethyl)-amino]propane 1-(7,8-Dimethoxy-1,3,4,5-tetrahydro-2H-3-benzazepin-2,4-dion-3-yl)-3-[N-methyl-N-(2-(pyridyl-3-N-oxide)-ethyl)-amino]-propane 1-(7,8-Dimethoxy-1,3,4,5-tetrahydro-2H-3-benzazepin-2,4-dion-3-yl)-3-[N-methyl-N-(2-(6,7-dimethoxyisoquinolyl-4-N-oxide)-ethyl)-amino]-propane 1-(7,8-Dimethoxy-1,3,4,5-tetrahydro-2H-3-benzazepin-1,2-dion-3-yl)-3-[N-methyl-N-(2-(pyridyl-3-N-oxide)-ethyl)-amino]-propane 1-(7,8-Dimethoxy-1,3,4,5-tetrahydro-2H-3-benzazepin-2-on-3-yl)-3-[N-methyl-N-(2-(6,7-dimethoxy-isoquinolyl-4-N-oxide)-ethyl)-amino]-propane 1-(7,8-Dimethoxy-1,3,4,5-tetrahydro-2H-3-benzazepin-1,2-dion-3-yl)-3-[N-methyl-N-(2-(pyridyl-3)-ethyl-amino]propane 1-(1-Hydroxy-7,8-dimethoxy-1,3,4,5-tetrahydro-2H-3-benzazepin-2-on-3-yl)-3-[N-methyl-N-(2-(pyridyl-3)-ethyl)-amino]propane 1-(7,8-Dimethoxy-1,3,4,5-tetrahydro-2H-3-benzazepin-2,4-dion-3-yl)-3-[N-methyl-N-(2-(pyridyl-3)-ethyl)-amino]propane 1-(7,8-Dimethoxy-1,3,4,5-tetrahydro-2H-3-benzazepin-2,4-dion-3-yl)-3-[N-methyl-N-(2-(6,7-dimethoxy-isoquinolyl-4)-ethyl)-amino]propane 1-(7,8-Dimethoxy-1,3,4,5-tetrahydro-2H-3-benzazepin-1,2-dion-3-yl)-3-[N-methyl-N-(2-(6,7-dimethoxy-isoquinolyl-4)-ethyl)-amino]propane 1-(7,8-Dimethoxy-1,3,4,5-tetrahydro-2H-3-benzazepin-2-on-3-yl)-3-[N-methyl-N-(3,5-dimethyl-isoxazolyl-4)-methyl)-amino]propane 1-(7,8-Dimethoxy-1,3,4,5-tetrahydro-2H-benzazepin-2-thion-3-yl)-3-[N-methyl-N-(2-(6-methoxy-benzo[b]thienyl-3)-ethyl)-amino]propane 1-(7,8-Dimethoxy-1,3,4,5-tetrahydro-2H-3-benzazepin-2-on-3-yl)-3-[N-benzyl-N-(2-(3-methyl-5-methoxy-benzo[b]furyl-3)-ethyl-amino]propane 1-(7,8-Dimethoxy-1,3,4,5-tetrahydro-2H-3-benzazepin-2-on-3-yl)-3-[N-((thienyl-2)-methyl-amino]propane 1-(7,8-Dimethoxy-1,3,4,5-tetrahydro-2H-3-benzazepin-2-on-3-yl)-3-[N-methyl-N-(2-(4-methoxy-benzo[b]furyl-3)-ethyl)-amino]propane 1-(7,8-Dimethoxy-1,3,4,5-tetrahydro-2H-3-benzazepin-2-on-3-yl)-3-[N-methyl-N-(2-(4,5,6,7-tetrahydro-benzo[b]thienyl-3)-ethyl)-amino]propane 1-(7,8-Dimethoxy-1,3,4,5-tetrahydro-2H-3-benzazepin-2-on-3-yl)-3-[N-methyl-N-(2-(6-hydroxy-benzo[b]thienyl-3)-ethyl-amino]propane 1-(7,8-Dimethoxy-1,3,4,5-tetrahydro-2H-3-benzazepin-2-on-3-yl)-3-[N-methyl-N-(2-(6-methylsulphonyloxy-benzo[b]thienyl-3)-ethyl)-amino]propane 1-(7,8-Dimethoxy-1,3,4,5-tetrahydro-2H-3-benzazepin-2-on-3-yl)-[N-methyl-N-(2-(6-ethoxycarbonylmethoxy-benzo[b]thienyl-3)-ethyl)-amino]propane 1-(7,8-Dimethoxy-1,3,4,5-tetrahydro-2H-3-benzazepin-2-on-3-yl)-3-[N-methyl-N-(2-(6-carboxymethoxy-benzo[b]thienyl-3)-ethyl)-amino]propane 1-(7,8-Dimethoxy-1,3,4,5-tetrahydro-2H-3-benzazepin-2-on-3-yl)-3-[N-methyl-N-(2-(benzo[b]thienyl-4)-ethyl)-amino]-propane 1-(7-Bromo-8-methoxy-1,3,4,5-tetrahydro-2H-3-benzazepin-2-on-3-yl)-3-[N-methyl-N-(4-(thienyl-2)-butyl-amino]propane 1-(7-Methoxy-1,3,4,5-tetrahydro-2H-3-benzazepin-2-on-3-yl)-3-[N-methyl-N-(2-(benzo[b]thienyl-3)-ethyl)-amino]propane 1-(1,3,4,5-Tetrahydro-2H-3-benzazepin-2-on-3-yl)-3-[N-methyl-N-(2-(6-methoxy-benzo[b]thienyl-3)-ethyl)-amino]propane 1-(7,8-Dimethyl-1,3,4,5-tetrahydro-2H-3-benzazepin-2-on-3-yl)-3-[N-methyl-N-(2-(benzo[b]furyl-2)-ethyl)-amino]propane 1-(7,8-Dimethyl-1,3,4,5-tetrahydro-2H-3-benzazepin-2-on-3-yl)-3-[N-methyl-N-(2-(benzo[b]thienyl-3)-ethyl)-amino]propane 1-(7,8-Dimethyl-1,3,4,5-tetrahydro-2H-3-benzazepin-2-on-3-yl)-3-[N-methyl-N-(2-(6-methoxy-benzo[b]thienyl-3)-ethyl)-amino]propane 1-(7,8-Dimethoxy-1,3,4,5-tetrahydro-2H-3-benzazepin-2-on-3-yl)-3-[N-methyl-N-(2-methyl-2-(benzo[b]thienyl-3)-ethyl)-amino]propane 1-(7,8-Dimethoxy-2,3-dihydro-1H-3-benzazepin-2-on-3-yl)-3-[N-methyl-N-(2-(2,5-dimethyl-thienyl-3)-ethyl)-amino]propane 1-(7,8-Dimethoxy-1,3,4,5-tetrahydro-2H-3-benzazepin-2-on-3-yl)-3-[N-methyl-N-(3-(2,5-dimethyl-thienyl-3)-propyl-amino]propane 1-(7,8-Dimethyl-1,3,4,5-tetrahydro-2H-3-benzazepin-2-on-3-yl)-3-[N-methyl-N-(2-(benzo[b]furyl-3)-ethyl)-amino]propane 1-(7,8-Dimethoxy-1,3,4,5-tetrahydro-2H-3-benzazepin-2-on-3-yl)-3-[N-methyl-N-(2-(6-acetamino-benzo[b]thienyl-3)-ethyl)-amino]propane 1-(7,8-Dimethyl-1,3,4,5-tetrahydro-2H-3-benzazepin-2-on-3-yl)-3-[N-methyl-N-(2-(6-methoxy-benzo[b]furyl-3)-ethyl)-amino]propane 1-(7,8-Methylenedioxy-1,3,4,5-tetrahydro-2H-3-benzazepin-2-on-3-yl)-3-[N-methyl-N-(2-(6-methoxy-benzo[b]furyl-3)-ethyl)-amino]propane 1-(7,8-Dimethoxy-1,3,4,5-tetrahydro-2H-3-benzazepin-2-on-3-yl)-3-[N-methyl-N-(2-(6-dimethylamino-benzo[b]thienyl-3)-ethyl)-amino]propane 1-(7,8-Dimethoxy-2,3-dihydro-1H-3-benzazepin-2-on-3-yl)-3-[N-methyl-N-(2-(benzo[b]furyl-3)-ethyl)-amino]propane 1-(7,8-Dimethoxy-1,3,4,5-tetrahydro-2H-3-benzazepin-2-on-3-yl)-3-[N-methyl-N-(3-(4,5,6,7-tetrahydro-benzo[b]thienyl-3)-propyl)-amino]propane 1-(7,8-Dimethoxy-1,3,4,5-tetrahydro-2H-3-benzazepin-2-thion-3-yl)-3-[N-methyl-N-(2-(benzo[b]thienyl-3)-ethyl)-amino]propane 1-(7,8-Dimethoxy-1,3,4,5-tetrahydro-2H-3-benzazepin-1,2-dion-3-yl)-3-[N-methyl-N-(2-(benzo[b]thienyl-3)-ethyl)-amino]propane 1-(7,8-Methylenedioxy-2,3-dihydro-1H-3-benzazepin-2-on-3-yl)-3-[N-methyl-N-(2-(6-methoxy-benzo[b]furyl-3)-ethyl)-amino]propane 1-(7,8-Methylenedioxy-2,3-dihydro-1H-3-benzazepin-2-on-3-yl)-3-[N-methyl-N-(2-(6-methoxy-benzo[b]thienyl-3)-ethyl)-amino]propane 1-(7,8-Dimethoxy-1,3,4,5-tetrahydro-2H-3-benzazepin-2-on-3-yl)-3-[N-methyl-N-(3-(6-methoxy-benzo[b]thienyl-3)propyl)-amino]propane 1-(7,8-Dimethyl-1,3,4,5-tetrahydro-2H-3-benzazepin-2-on-3-yl)-3-[N-methyl-N-(4-(2,5-dimethyl-thienyl-3)-butyl)-amino]propane 1-(7,8-Dimethoxy-2,3-dihydro-1H-3-benzazepin-2-n-3-yl)-3-[N-methyl-N-(2-(4,5,6,7-tetrahydro-benzo[b]thienyl-3)-ethyl)-amino]propane 1-(7,8-Methylenedioxy-1,3,4,5-tetrahydro-2H-3-benzazepin-2-on-3-yl)-3-[N-methyl-N-(4-(2,5-dimethyl-thienyl-3)-butyl)-amino]propane 1-(7,8-Ethylenedioxy-1,3,4,5-tetrahydro-2H-3-benzazepin-2-on-3-yl)-3-[N-methyl-N-(2-(6-methoxy-benzo[b]furyl-3)-ethyl)-amino]propane 1-(7,8-Dimethoxy-1,3,4,5-tetrahydro-2H-3-benzazepin-2-on-3-yl)-3-[N-methyl-N-(2-(6-acetamino-benzo[b]thienyl-3)-ethyl)-amino]propane 1-(7,8-Dimethoxy-2,3-dihydro-1H-3-benzazepin-2-on-3-yl)-3-[N-methyl-N-(2-(benzo[b]furyl-2)-ethyl)-amino]propane 1-(7,8-Dimethoxy-1,3,4,5-tetrahydro-2H-3-benzazepin-2-on-3-yl)-3-[N-methyl-N-[5-(thienyl-2)-pentyl)-amino]propane 1-(7,8-Methylenedioxy-1,3,4,5-tetrahydro-2-H-3-benzazepin-2-thion-3-yl)-3-[N-methyl-N-(2-(6-methoxy-benzo[b]furyl-3)-ethyl)-amino]propane 1-(7,8-Dimethoxy-1,3,4,5-tetrahydro-2H-3-benzazepin-1,2-dion-3-yl)-3-[N-methyl-N-(2-(6-methoxy-benzo[b]thienyl-3)-ethyl)-amino]propane 1-(7,8-Dimethyl-1,3,4,5-tetrahydro-2H-3-benzazepin-2-thion-3-yl)-3-[N-methyl-N-(2-(6-methoxy-benzo[b]furyl-3)-ethyl)-amino]propane 1-(7,8-Dimethyl-1,3,4,5-tetrahydro-2H-3-benzazepin-2-thion-3-yl)-3-[N-methyl-N-(2-(benzo[b]furyl-2)-ethyl)-amino]propane 1-(7,8-Dimethoxy-1,3,4,5-tetrahydro-2H-3-benzazepin-2-on-3-yl)-3-[N-methyl-N-(2-(3-phenyl-5-methoxy-benzo[b]furyl-2)-ethyl)-amino]propane 1-(7,8-Dimethoxy-1,3,4,5-tetrahydro-2H-3-benzazepin-2-on-3-yl)-3-[N-allyl-N-(2-(benzo[b]furyl-2)-ethyl)-amino]propane 1-(7,8-Dimethoxy-2,3-dihydro-1H-3-benzazepin-2-on-3-yl)-3-[N-methyl-N-(2-(6-methylsulphonyloxy-benzo[b]thienyl-3)-ethyl)-amino]propane 1-(7,8-Methylenedioxy-1,3,4,5-tetrahydro-2H-3-benzazepin-2-on-3-yl)-3-[N-methyl-N-(2-(benzo[b]thienyl-3)-ethyl)-amino]propane 1-(7,8-Dimethoxy-1,3,4,5-tetrahydro-2H-3-benzazepin-2-on-3-yl)-3-[N-methyl-N-(2-(6-methylsulphonyloxy-benzo[b]thienyl-3)-ethyl)-amino]propane 1-(7,8-Dimethoxy-1,3,4,5-tetrahydro-2H-3-benzazepin-2-on-3-yl)-3-[N-methyl-N-(4-(2,5-dimethyl-thienyl-3)-butyl)-amino]propane 1-(7,8-Dimethoxy-2,3-dihydro-1H-3-benzazepin-2-on-3-yl)-3-[N-methyl-N-(2-(6-methoxy-benzo[b]thienyl-3)-ethyl)-amino]propane 1-(7,8-Dimethoxy-1,3,4,5-tetrahydro-2H-3-benzazepin-2-on-3-yl)-3-[N-methyl-N-(2-(3-methyl-5-methoxy-benzo[b]furyl-2)-ethyl)-amino]propane 1-(7,8-Dimethoxy-1,3,4,5-tetrahydro-2H-3-benzazepin-2-on-3-yl)-3-[N-ethyl-N-(2-(6-methoxy-benzo[b]thienyl-3-ethyl)-amino]propane 1-(7,8-Methylenedioxy-1,3,4,5-tetrahydro-2H-3-benzazepin-1,2-dion-3-yl)-3-[N-methyl-N-(2-(6-methoxy-benzo[b]thienyl-3)-ethyl)-amino]propane 1-(7,8-Dimethyl-2,3-dihydro-1H-3-benzazepin-2-on-3-yl)-3-[N-methyl-N-(2-(6-methoxy-benzo[b]furyl-3)-ethyl)-amino]propane 1-(7,8-Dimethyl-2,3-dihydro-1H-3-benzazepin-2-on-3-yl)-3-[N-methyl-N-(2-(benzo[b]furyl-2)-ethyl)-amino]propane 1-(7,8-Dimethyl-2,3-dihydro-1H-3-benzazepin-2-on-3-yl)-3-[N-methyl-N-(2-(benzo[b]thienyl-3)-ethyl)-amino]propane 1-(7,8-Dimethoxy-1,3,4,5-tetrahydro-2H-3-benzazepin-2-on-3-yl)-3-[N-methyl-N-(2-(benzo[b]thienyl-2)-ethyl)-amino]propane 1-(7,8-Dimethoxy-1,3,4,5-tetrahydro-2H-3-benzazepin-2-on-3-yl)-4-[N-methyl-N-(2-(benzo[b]thienyl-3)-ethyl)-amino]butane 1-(7,8-Dimethoxy-2,3-dihydro-1H-3-benzazepin-2-on-3-yl)-3-[N-methyl-N-(2-(6-carboxymethoxy-benzo[b]thienyl-3)-ethyl)-amino]propane 1-(7,8-Dimethyl-1,3,4,5-tetrahydro-2H-3-benzazepin-1,2-dion-3-yl)-3-[N-methyl-N-(2-(6-methoxy-benzo[b]thienyl-3)-ethyl)-amino]propane 1-(7,8-Methylenedioxy-1,3,4,5-tetrahydro-2H-3-benzazepin-2-on-3-yl)-3-[N-methyl-N-(2-(6-methoxy-benzo[b]thienyl-3)-ethyl)-amino]propane 1-(7,8-Dimethoxy-1,3,4,5-tetrahydro-2H-3-benzazepin-2-on-3-yl)-3-[N-methyl-N-(2-(6-carboxymethoxy-benzo[b]thienyl-3)-ethyl)-amino]propane 1-(7,8-Dimethoxy-1,3,4,5-tetrahydro-2H-3-benzazepin-2-on-3-yl)-3-[N-methyl-N-[2-(7-methoxy-benzo[b]thienyl-3)-ethyl)-amino]propane 1-(7,8-Methylenedioxy-1,3,4,5-tetrahydro-2H-3-benzazepin-2-thion-3-yl)-3-[N-methyl-N-(2-(benzo[b]thienyl-3)-ethyl)-amino]propane 1-(7,8-Methylenedioxy-1,3,4,5-tetrahydro-2H-3-benzazepin-1,2-dion-3-yl)-3-[N-methyl-N-(2-(6-methoxy-benzo[b]furyl-3)-ethyl)-amino]propane 1-(7,8-Dimethyl-2,3-dihydro-1H-3-benzazepin-2-on-3-yl)-3-[N-methyl-N-(2-(6-methoxy-benzo[b]thienyl-3)-ethyl)-amino]propane 1-(7,8-Methylenedioxy-2,3-dihydro-1H-3-benzazepin-2-on-3-yl)-3-[N-methyl-N-(2-(benzo[b]thienyl-3)-ethyl)-amino]propane 1-(7,8-Dimethoxy-1,3,4,5-tetrahydro-2H-3-benzazepin-2-on-3-yl)-3-[N-methyl-N-(2-(6-methoxy-benzo[b]thienyl-2)-ethyl)-amino]propane 1-(7,8-Dimethoxy-1,3,4,5-tetrahydro-2H-3-benzazepin-2-on-3-yl)-2-[N-methyl-N-(2-(thienyl-2)-ethyl)-amino]ethane 1-(7,8-Dimethoxy-2,3-dihydro-1H-3-benzazepin-2-on-3-yl)-3-[N-methyl-N-(2-(6-ethoxycarbonylmethoxy-benzo[b]thienyl-3)-ethyl)-amino]propane 1-(7,8-Methylenedioxy-1,3,4,5-tetrahydro-2H-3-benzazepin-2-on-3-yl)-3-[N-methyl-N-(2-benzo[b]furyl-2)-ethyl)-amino]propane 1-(7,8-Methylenedioxy-1,3,4,5-tetrahydro-2H-3-benzazepin-2-on-3-yl)-3-[N-methyl-N-(2-(benzo[b]furyl-3)-ethyl)-amino]propane 1-(7,8-Dimethoxy-1,3,4,5-tetrahydro-2H-3-benzazepin-2-on-3-yl)-3-[N-methyl-N-(2-(6-ethoxycarbonylmethoxy-benzo[b]thienyl-3)-ethyl)-amino]propane 1-(7,8-Dimethoxy-2,3-dihydro-1H-3-benzazepin-2-on-3-yl)-3-[N-methyl-N-(2-(6-methoxy-benzo[b]furyl-3)-ethyl)-amino]propane 1-(7,8-Dimethoxy-1,3,4,5-tetrahydro-2H-3-benzazepin-2-on-3-yl)-3-[N-methyl-N-[2-(6-methylsulphonyloxy-benzo[b]furyl-3)-ethyl)-amino]propane 1-(7,8-Methylenedioxy-1,3,4,5-tetrahydro-2H-3-benzazepin-2-thion-3-yl)-3-[N-methyl-N-(2-(6-methoxy-benzo[b]thienyl-3)-ethyl)-amino]propane 1-(7,8-Methylenedioxy-1,3,4,5-tetrahydro-2H-3-benzazepin-1,2-dion-3-yl)-3-[N-methyl-N-(2-(benzo[b]furyl-2)-ethyl)-amino]propane 1-(7,8-Methylenedioxy-2,3-dihydro-1H-3-benzazepin-2-on-3-yl)-3-[N-methyl-N-(2-(benzo[b]furyl-2)-ethyl)-amino]propane 1-(7,8-Dimethyl-1,3,4,5-tetrahydro-2H-3-benzazepin-2-thion-3-yl)-3-[N-methyl-N-(2-(6-methoxy-benzo[b]thienyl-3)-ethyl)-amino]propane 1-(7,8-Dimethyl-1,3,4,5-tetrahydro-2H-3-benzazepin-2-thion-3-yl)-3-[N-methyl-N-(2-(benzo[b]thienyl-3)-ethyl)-amino]propane 1-(7,8-Dimethoxy-1,3,4,5-tetrahydro-2H-3-benzazepin-2-thion-3-yl)-3-[N-methyl-N-(2-(benzo[b]furyl-2)-ethyl-amino]propane 1-(7,8-Dimethoxy-1,3,4,5-tetrahydro-2H-3-benzazepin-2-thion-3-yl)-3-[N-methyl-N-(2-(6-methoxy-benzo[b]furyl-3)-ethyl)-amino]propane 1-(7,8-Dimethoxy-1,3,4,5-tetrahydro-2H-3-benzazepin-2-on-3-yl)-3-[N-methyl-N-(2-(4-nitro-pyridyl-2)-ethyl)-amino]propane 1-(7,8-Dimethoxy-1,3,4,5-tetrahydro-2H-3-benzazepin-2-on-3-yl)-3-[N-methyl-N-(2-(4-amino-pyridyl-2)-ethyl)-amino]propane 1-(7,8-Dimethoxy-1,3,4,5-tetrahydro-2H-3-benzazepin-2-on-3-yl)-3-[N-methyl-N-(2-(4-acetylamino-pyridyl-2)-ethyl)-amino]propane 1-(7,8-Dimethoxy-1,3,4,5-tetrahydro-2H-3-benzazepin-2-on-3-yl)-3-[N-methyl-N-(2-(4-carbamoylamino-pyridyl-2)-ethyl)-amino]propane 1-(7,8-Dimethoxy-1,3,4,5-tetrahydro-2H-3-benzazepin-2-on-3-yl)-3-[N-methyl-N-(2-(4-N-methyl-carbamoylaminopyridyl-2)-ethyl)-amino]propane 1-(7,8-Dimethoxy-1,3,4,5-tetrahydro-2H-3-benzazepin-2-on-3-yl)-3-[N-methyl-N-(2-(6,7-dimethoxyquinolyl-4)-ethyl)-amino]propane 1-(7,8-Dimethoxy-1,3,4,5-tetrahydro-2H-3-benzazepin-2-on-3-yl)-3-[N-methyl-N-(2-(N-methyl-pyrrolyl-3)-ethyl)-amino]propane 1-(7,8-Dimethoxy-1,3,4,5-tetrahydro-2H-3-benzazepin-2-on-3-yl)-3-[N-methyl-N-(2-(pyrrolyl-3)-ethyl)-amino]propane 1-(7,8-Dimethoxy-1,3,4,5-tetrahydro-2H-3-benzazepin-2-on-3-yl)-3-[N-methyl-N-(2-(3-methyl-isoxazoly-5)-ethyl)-amino]propane 1-(7,8-Dimethoxy-1,3,4,5-tetrahydro-2H-3-benzazepin-2-on-3-yl)-3-[N-methyl-N-(2-(isoxazolyl-3)-ethyl)-amino]propane 1-(7,8-Dimethoxy-1,3,4,5-tetrahydro-2H-3-benzazepin-2-on-3-yl)-3-[N-methyl-N-(2-(oxazolyl-4)-ethyl)-amino]propane 1-(7,8-Dimethoxy-1,3,4,5-tetrahydro-2H-3-benzazepin-2-on-3-yl)-3-[N-methyl-N-(2-(oxazolyl-5)-ethyl)-amino]propane 1-(7,8-Dimethoxy-1,3,4,5-tetrahydro-2H-3-benzazepin-2-on-3-yl)-3-[N-methyl-N-(2-(pyrazolyl-3)-ethyl)-amino]propane 1-(7,8-Dimethoxy-1,3,4,5-tetrahydro-2H-3-benzazepin-2-on-3-yl)-3-[[N-methyl-N-(2-(1,3-dimethyl-pyrazolyl-5)-ethyl)-amino]propane However, the preferred compounds are the compounds of formula Ia:

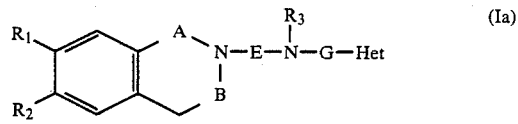

wherein

A represents a —CH$_2$—CH$_2$—, —CH=CH—,

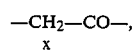

—CO—CO— or

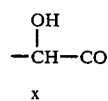

group and B represents a methylene group or A represents a —CH$_2$—CH$_2$— or —CH=CH— group and B represents a carbonyl or thiocarbonyl group, in which the carbon atom designated x is in each case linked to the phenyl nucleus, E represents an n-propylene group, G represents an ethylene, n-propylene or n-butylene group, R₁ represents a chlorine or bromine atom or a methyl, methoxy, nitro, amino, methylamino or dimethylamino group, R₂ represents a chlorine or bromine atom or a methyl or methoxy group or R₁ and R₂ together represent a methylenedioxy or ethylenedioxy group, R₃ represents a hydrogen atom or a methyl, ethyl or allyl group and Het represents a pyrrolyl-2-, pyrrolyl-3-, N-methyl-pyrrolyl-2-, N-methyl-pyrrolyl-3-, furyl-2-, benzo[b]furyl-2-, benzo[b]furyl-3-, 7-methyl-benzo[b]furyl-3-, 6-methoxy-benzo[b]furyl-3-, 5-methoxy-3-phenyl-benzo[b]furyl-2-, thienyl-2-, thienyl-3-, 5-methylthienyl-2-, 2,5-dimethyl-thienyl-3-, 5-bromothienyl-2-, benzo[b]thienyl-2-, benzo[b]thienyl-3-, 6-hydroxy-benzo[b]thienyl-3-, 6-methoxy-benzo[b]thienyl-3-, 5,6-dimethoxy-benzo[b]thienyl-3-, 2,5-dimethyl-benzo[b]thienyl-3-, 5-methoxy-benzo[b]thienyl-2-, 6-methoxy-benzo[b]thienyl-2-, 6-methylmercapto-benzo[b]thienyl-3-, 6-methylsulfinyl-benzo[b]thienyl-3-, 6-methylsulfonyl-benzo[b]thienyl-3-, 6-methylsulfonyloxy-benzo[b]thienyl-3-, 6-ethoxycarbonylmethoxy-benzo[b]thienyl-3-, 6-carboxymethoxy-benzo[b]thienyl-3-, 6-dimethylamino-benzo[b]thienyl-3-, 6-methylsulfonylamino-benzo[b]thienyl-3-, 6-acetamino-benzo[b]-thienyl-3-, benzo[b]thienyl-4-, pyrazolyl-1-, pyrazolyl-3-, 1,5-dimethyl-pyrazolyl-3-, 1-methylimidazolyl-4-, 2-(3,4-dimethoxy-phenyl)-imidazolyl-4(5)-, benzo[d]imidazolyl-1-, 2-benzyl-benzo[d]imidazolyl-1-, imidazo[1,2-a]pyridyl-3-, oxazolyl-4-, oxazolyl-5-, isoxazolyl-3-, 3-methyl-isoxazolyl-5-, 4-methyl-thiazolyl-5-, pyridyl-2-, pyridyl-3-, pyridyl-4-, pyridyl-3-N-oxide, 4-nitro-pyridyl-2-, 4-amino-pyridyl-2-, 4-acetylaminopyridyl-2-, 4-carbamoylamino- pyridyl-2-, 4-N-methylcarbamoylamino-pyridyl-2-, 6,7-dimethoxy-quinolyl-4-, 6,7-dimethoxy isoquinolyl-4-, or 6,7-dimethoxy-isoquinolyl-4-N-oxide group, and the acid addition salts thereof, particularly the nontoxic, pharmaceutically acceptable acid addition salts thereof with inorganic or organic acids.

However, particularly preferred compounds of formula Ia are those wherein

A represents a —CH₂—CH₂— or —CH=CH— group and B represents a carbonyl or thiocarbonyl group, E represents an n-propylene group, G represents an ethylene, n-propylene or n-butylene group, R₁ and R₂ each represent a methoxy group or R₁ and R₂ together represent a methylenedioxy group, R₃ represents a hydrogen atom or a methyl group and Het represents a pyrroly-2-, pyrrolyl-3-, N-methyl-pyrrolyl-2-, N-methyl-pyrrolyl-3-, thienyl-2-, thienyl-3-, 5-methyl-thienyl-2-, 2,5-dimethyl-thienyl-3-, 5-bromo-thienyl-2-, pyrazolyl-1-, pyrazolyl-3-, 1-methylimidazolyl-4-, isoxazolyl-3-, benzo[b]furyl-2-, benzo[b]furyl-3, 7-methyl-benzo[b]furyl-3-, 6-methoxy-benzo-[b]furyl-3-, 7-methoxy-benzo[b]furyl-3-, benzo[b]thienyl-2-, benzo[b]thienyl-3-, 6-methoxybenzo[b]thienyl-3-, 6-methylsulfonyloxy-benzo[b]thienyl-3-, 6-ethoxycarbonylmethoxy-benzo[b]thienyl-3-, 6-carboxymethoxy-benzo[b]thienyl-3-, 6-acetamino-benzo[b]thienyl-3-, benzo[d]imidazolyl-1-, imidazo-[1,2-a]pyridyl-3- or pyridyl group, and the acid addition salts thereof, particularly the nontoxic, pharmaceutically acceptable acid addition salts thereof with inorganic or organic acids.

According to the invention, the new compounds are obtained by the following processes:

(a) A compound of formula II:

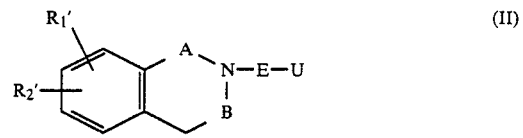

can be reacted with a compound of formula III:

wherein

A, B, E, G and Het are as hereinbefore defined,

R₁' represents a hydroxy, amino or alkylamino group protected by a protecting group or has the meanings given for R₁ hereinbefore, R₂' represents a hydroxy group protected by a protecing group or has the meanings given for R₂ hereinbefore, one of the groups U or V represents the R₃' —NH—group, wherein R₃' represents a protecting group for an amino group or has the meanings given for R₃ hereinbefore and the other group U or V represents a nucleophilically exchangeable group such as a halogen atom or a sulphonyloxy group, e.g. a chlorine, bromine or iodine atom or a methanesulphonyloxy, p-toluenesulphonyloxy or ethoxysulphonyloxy group, with any protecting group used subsequently being split off.

Suitable protecting groups for a hydroxy group include, for example, trimethylsilyl, acetyl, benzoyl, benzyl and tetrahydropyranyl groups and suitable protecting groups for an amino or alkylamino group include the acetyl, benzoyl, ethoxycarbonyl and benzyl groups.

The reaction is conveniently carried out in a solvent or mixture of solvents such as acetone, diethylether, methylformamide, dimethylformamide, dimethylsulfoxide, benzene, toluene, chlorobenzene, tetrahydrofuran, benzene/tetrahydrofuran, dioxan or in an excess of the compounds of formulae II and/or III used and optionally in the presence of an acid binding agent, e.g. an alkoxide such as potassium tert.butoxide, an alkali metal hydroxide such as sodium or potassium hydroxide, an alkali metal carbonate such as potassium carbonate, an alkali metal amide such as sodium amide, an alkali metal hydride such as sodium hydride, a tertiary organic base such as triethylamine or pyridine, in which the latter can simultaneously also serve as solvent, or a reaction accelerator such as potassium iodide depending on the reactivity of the nucleophilically exchangeable group, conveniently at temperatures of between 0° and 150° C., preferably at temperatures of between 50° and 120° C., e.g. at the boiling temperature of the solvent used. However the reaction can also be carried out without a solvent. It is, however, particularly advantageous to perform the reaction in the presence of a tertiary organic base or an excess of the amine of formula III.

The optionally subsequent splitting off of a protected group used is preferably carried out by hydrolysis in an aqueous solvent, e.g. in water, isopropanol/water tetrahydrofuran/water or dioxan/water, in the presence of an acid such as hydrochloric or sulphuric acid or in the presence of an alkali metal base such as sodium hydroxide or potassium hydroxide at temperatures of between 0° and 100° C., preferably at the boiling temperature of the reaction mixture. However, a benzyl group is preferably split off by hydrogenolysis, e.g. with hydrogen in the presence of a catalyst such as palladium/charcoal in a solvent such as methanol, ethanol, ethylacetate or glacial acetic acid, optionally with the addition of an acid such as hydrochloric acid at temperatures of between 0° and 50° C., but preferably at ambient temperature, under a hydrogen pressure of from 1 to 7 bar, preferably from 3 to 5 bar.

(b) Compounds of formula I wherein A represents a —CH$_2$—CH$_2$— group, B represents a methylene or carbonyl group and R$_3$ does not represent an alkenyl group having 3 to 5 carbon atoms can be prepared by hydrogenating a compound of formula IV:

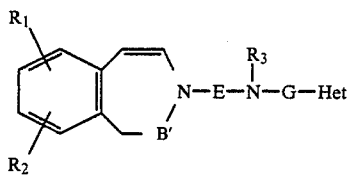
(IV)

wherein

R$_1$ to R$_3$, E, G and Het are as hereinbefore defined and B' represents a methylene or carbonyl group.

The hydrogenation is carried out in a solvent or mixture of solvents such as methanol, ethanol, ethylacetate or glacial acetic acid with catalytically activated hydrogen, e.g. with hydrogen in the presence of platinum or palladium/charcoal, under a hydrogen pressure of from 1 to 7 bar, preferably from 3 to 5 bar, and at temperatures of between 0° and 75° C. but preferably at temperatures of between 20° and 50° C.

If in a compound of formula I, R$_3$ represents an alkenyl group, this is simultaneously converted during the reduction, into the corresponding alkyl group or, if R$_1$ and/or R$_2$ represents a benzyloxy group, this is converted during the reduction to the corresponding hydroxy group.

(c) Compounds of formula I wherein B represents a thiocarbonyl group can be prepared by reacting a compound of formula V:

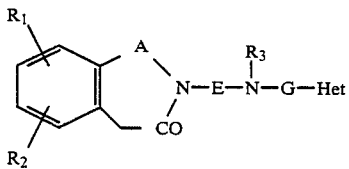
(V)

wherein

R$_1$ to R$_3$, A, E, G and Het are as hereinbefore defined, with a sulphurizing agent.

The reaction is carried out with a sulphurizing agent such as phosphorus pentasulphide, 2,4-bis(4-methoxyphenyl)-1,3-dithia-2,4-diphosphetan-2,4-disulfide or 2,4-bis(methylthio)-1,3-dithia-2,4-diphosphetan-2,4-disulfide conveniently in a solvent such as toluene or xylene at temperatures of between 50° and 150° C., e.g. at the boiling temperature of the reaction mixture.

(d) Compounds of formula I wherein A represents a

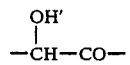

group can be prepared by reduction of a compound of formula VI:

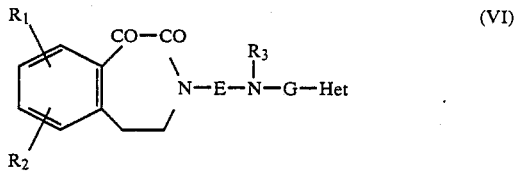
(VI)

wherein

R$_1$ to R$_3$, E, G and Het are as hereinbefore defined.

The reaction is carried out in the presence of a suitable reducing agent such as a metal hydride, e.g. sodium borohydride, in a suitable solvent such as water/methanol or methanol/ether at temperatures of between 0° and 80° C., but preferably at temperatures of between 15° and 40° C.

(e) Compounds of formula I wherein A represents a —CH$_2$—CH$_2$— or —CH=CH—group and B represents a methylene group can be prepared by reduction of a compound of formula VII:

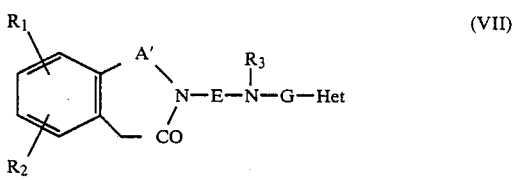
(VII)

wherein

R$_1$ to R$_3$, E, G and Het are as hereinbefore defined and A' represents a —CH$_2$—CH$_2$— or —CH=CH— group.

The reduction is preferably carried out with a metal hydride such as lithium aluminium hydride or diborane or with a complex of borane and a thioether, e.g. with a borane-dimethylsulfide complex, in a suitable solvent such as diethyl ether or tetrahydrofuran at temperatures between 0° and 50° C., but preferably at temperatures of between 10° and 25° C.

(f) Compounds of formula I wherein A represents the —COCO— group can be prepared by oxidation of a compound of formula VIII:

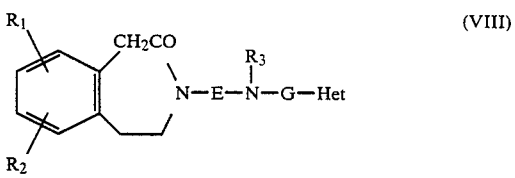
(VIII)

wherein

R$_1$ to R$_3$, E, G and Het are as hereinbefore defined.

The oxidation is preferably carried out with an oxidizing agent such as potassium permanganate, selenium dioxide or sodium dichromate in a suitable solvent or mixture of solvents such as water, water/dioxan, glacial acetic acid, water/glacial acetic acid or acetic anhydride at temperatures of between 0° and 100° C., preferably at temperatures of between 20° and 80° C.

(g) Compounds of formula I can also be prepared by reacting compound of formula IX:

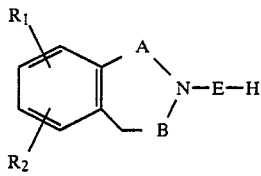

wherein

A, B, E, $R_1$ and $R_2$ are as hereinbefore defined, but in the group E two hydrogen atoms in a —$CH_2$— or —$CH_3$— group of the group E are replaced by an oxygen atom, with a compound of formula X:

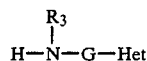

wherein $R_3$, G and Het are as hereinbefore defined, in the presence of a reducing agent.

The reaction is conveniently carried out in a suitable solvent or mixture of solvents such as methanol, ethanol, ethanol/ethyl acetate or dioxan at temperatures of between 0° and 100° C., but preferably at temperatures of between 20° and 80° C.

It is particularly advantageous to carry out reductive amination in the presence of a complex metal hydride such as sodium borohydride, lithium or sodium cyanoborohydride, preferably at a pH of 6–7 and at ambient temperature or in the presence of palladium/charcoal under a hydrogen pressure of 5 bar. Any benzyl groups present can simultaneously be split off by hydrogenolysis and/or any double bonds can be hydrogenated.

(h) Compounds of formula I can also be prepared by reacting a compound of formula XI:

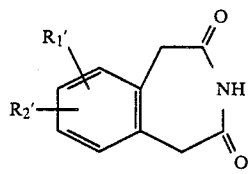

wherein $R_1'$ represents a hydroxy, amino or alkylamino group protected by a protecting group or has the meanings given for $R_1$ hereinbefore, and $R_2'$ represents a hydroxy group protected by a protecting group or has the meanings given for $R_2$ hereinbefore, with a compound of formula XII:

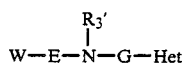

wherein

E, G and Het are as hereinbefore defined, $R_3'$ represents a protecting group for an amino group or has the meanings given for $R_3$ hereinbefore, and W represents a nucelophilically exchangeable group such as a halogen atom or a sulphonyloxy group, e.g. a chlorine, bromine or iodine atom or a methane-sulphonyloxy, p-toluenesulphonyloxy or ethoxysulphonyloxy group, optionally with any protecting group used subsequently being split off.

Suitable protecting groups for a hydroxy group include, for example, the trimethylsilyl, acetyl, benzoyl, benzyl and tetrahydropyranyl groups and suitable protecting groups for an amino or alkyl-amino group include the acetyl, benzoyl, ethoxycarbonyl and benzyl groups.

The reaction is convently carried out in a solvent or mixture of solvents such as methylformamide, dimethylformamide, dimethylsulfoxide, benzene, chlorobenzene, tetrahydrofuran, benzene/tetrahydrofuran or dioxan in the presence of an acid binding agent, e.g. an alkoxide such as potassium tert.butoxide, an alkali metal hydroxide such as sodium or potassium hydroxide, an alkali metal carbonate such as potassium carbonate, an alkali metal amide such as sodium amide or an alkali metal hydride such as sodium hydride, conveniently at temperatures of between 0° and 150° C., preferably at temperatures of between 0° and 150° C.

The optional subsequent splitting off of any protecting group used is preferably carried out hydrolytically in an aqueous solvent, e.g. in water, isopropanol/water, tetrahydrofuran/water or dioxan/water, in the presence of an acid such as hydrochloric or sulphuric acid or in the presence of an alkali metal base such as sodium hydroxide or potassium hydroxide at temperatures of between 0° and 100° C., preferably at the boiling temperature of the reaction mixture. However, a benzyl group is preferably split off by hydrogenolysis, e.g. with hydrogen in the presence of a catalyst such as palladium/charcoal in a solvent such as methanol, ethanol, ethyl acetate or glacial acetic acid, optionally with the addition of an acid such as hydrochloric acid at temperatures of between 0° and 50° C., but preferably at ambient temperature, under a hydrogen pressure of from 1 to 7 bar, preferably from 3 to 5 bar.

The compounds of formula I can also be converted into the acid addition salts thereof, particularly the nontoxic, pharmaceutically acceptable acid addition salts thereof with inorganic or organic acids. Suitable acids include, for example, hydrochloric, hydrobromic, sulphuric, phosphoric, acetic, lactic, citric, tartaric, succinic, maleic and fumaric acids.

The compounds of formulae II to XII used as starting materials are known from the literature in some cases or can be obtained using methods known per se.

Thus, for example, a starting compound of formula II is obtained by reacting a corresponding benzazepine with a corresponding halogen compound and optionally by subsequently reacting with a corresponding amine. The corresponding benzazepine unsubstituted in the 3-position which is required for this is obtained by cyclizing a corresponding compound, e.g. by cyclizing a compound of formula XIII:

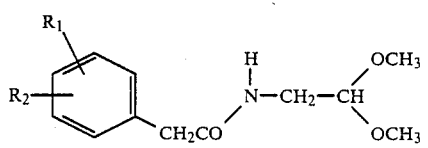

or a compound of formula

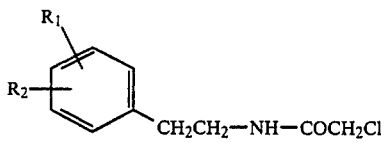

(XIV)

optionally followed by catalytic hydrogenation and/or reduction of the carbonyl group, for example with sodium borohydride/glacial acetic acid (see EP-Al-0,007,070) and/or oxidation, e.g. with selenium dioxide.

A compound of formulae IV to VIII used as starting material is preferably obtained by reacting a corresponding halogen compound with a corresponding amine, optionally followed by the splitting off of protecting groups used to protect hydroxy and/or amino groups.

A compound of formula IX is obtained, for example, by reacting a corresponding benzazepine unsubstituted in the 3-position with a corresponding haloacetal or haloketal, followed by hydrolysis.

As already mentioned hereinbefore, the new compounds of formula I and the nontoxic, pharmaceutically acceptable acid addition salts thereof with inorganic or organic acids have valuable pharmacological properties, particularly a long-lasting lowering effect on heart rate and the effect of reducing the $O_2$ requirement of the heart.

For example, the following compounds:
A = 1-(7,8-Dimethoxy-1,3,4,5-tetrahydro-2H-3-benzazepin-2-on-3-yl)-3-[N-methyl-N-(2-benzo[b]thienyl-3)-ethyl)-amino]-propane-hydrochloride,
B = 1-(7,8-Dimethoxy-1,3,4,5-tetrahydro-2H-3-benzazepin-2-on-3-yl)-3-[N-methyl-N-(2(6-methoxy-benzo[b]thienyl-3)-ethyl)-amino]-propane-hydrochloride, and
C = 1-(7,8-Dimethoxy-1,3,4,5-tetrahydro-2H-3-benzazepin-2-on-3-yl)-3-[N-methyl-N-(2-(benzo[b]furyl-2)-ethyl)-amino]-propane-hydrochloride
demonstrate biological properties as follows.
Effect on heart rate in rats:

The effect of the test substances on heart rate is investigated, for each dosage, on 2 to 4 rats with an average weight of 250–300 g. The rats are anaesthetized with pentobarbital (50 mg/kg i.p. and 20 mg/kg s.c.). The test substances are injected into the jugular vein in aqueous solution (0.1 ml/100 g).

The blood pressure is measured using a cannula tied into the carotid artery and the heart rate is recorded from an ECG obtained with needle electrodes (II or III derivation). The heart rate of the animals in the control period is between 330 and 420 beats/minute (b/min).

The following table contains the values found:

| Substance | Dosage [mg/kg] | Reduction in heart rate [%], measured t minutes after administration of substance | |
|---|---|---|---|
| | | t = 5 | t = 20 |
| A | 5 | 66 | 52 |
| B | 5 | 67 | 60 |
| C | 2.5 | 47 | 36 |

No toxic side effects are observed in the pharmacological tests. The new compounds are well tolerated.

The compounds according to the invention are suitable for the treatment of sinus tachycardia of various origins and for the prevention and treatment of ischaemic heart disease.

The dosage is conveniently from 0.03 to 1 mg/kg of body weight, preferably from 0.07 to 0.5 mg/kg of body weight, once or twice a day. The compounds of formula I and the nontoxic, pharmaceutically acceptable acid addition salts thereof with inorganic or organic acids can be incorporated, optionally together with other active substances, with one or more inert conventional carriers and/or diluents, e.g. with corn starch, lactose, glucose, microcrystalline cellulose, magnesium stearate, polyvinylpyrrolidone, citric acid, tartaric acid, water, water/ethanol, water/glycerol, water/sorbitol, water/polyethyleneglycol, propyleneglycol, carboxymethylcellulose or fatty substances such as hard fat or suitable mixtures thereof, to produce conventional galenic preparations such as tablets, coated tablets, capsules, powders, suspensions, drops, ampoules, syrups or suppositories.

The following Examples further illustrate the invention:
Preparation of the starting compounds:

EXAMPLE A 7,8-Dimethoxy-1,3-dihydro-2H-3-benzazepin-2-one (a) 3,4-Dimethoxy-phenylacetic acid chloride First, thionyl chloride (600 ml) is added dropwise with stirring over a period of 2 hours to a suspension of 3,4-dimethoxy-phenylacetic acid (549.4 g) in methylene chloride (600 ml). After the evolution of gas has ended (16 hours) the mixture is refluxed for a further hour. After the volatile components have been eluminated the residue is distilled in vacuo.
Yield: 486 g,
Bp: 134°–136° C./1.95 mbar (b) N-(2,2-Dimethoxyethyl)-3,4-dimethoxy-phenylacetamide While cooling with ice, a solution of 3,4-dimethoxy-phenylacetic acid chloride (485.2 g) in methylene chloride (1.1 liters) is added dropwise at 15°–20° C. to a solution of aminoacetaldehyde dimethylacetal (246.2 ml) and triethylamine (315 ml) in methylene chloride (2.2 liters) and the resulting mixture is stirred for 1 hour at 16°–18° C. It is then extracted several times with water, dried over magnesium sulphate and concentrated by evaporation. The resulting oil slowly crystallizes out.
Yield: 608 g,
Melting point: 66°–69° C.

(c) 7,8-Dimethoxy-1,3-dihydro-2H-3-benzazepin-2-one

A solution of N-(2,2-dimethoxyethyl)-3,4-dimethoxy-phenylacetamide (600.6 g) in concentrated hydrochloric acid (3 liters) is mixed with acetic acid (3 liters). After standing for 17 hours at ambient temperature the mixture is poured onto ice. The precipitated crystals are suction filtered, washed with water until neutral and dried.
Yield: 350 g,
Melting point: 234°–237° C.

EXAMPLE B 7,8-Dimethoxy-1,3,4,5-tetrahydro-2H-3-benzazepin-2-one

A suspension of 7,8-dimethoxy-1,3-dihydro-2H-3-benzazepin-2-one (21.9 g, 0.1 mol) and 10% palladium/-charcoal (1.5 g) in glacial acetic acid (200 ml) is hydrogenated at 50° C. under a hydrogen pressure of 5 bar. After the catalyst has been filtered off the solvent is evaporated in vacuo and the residue is taken up in methylene chloride. After extraction with sodium bicarbonate solution and washing with water, the product is dried over magnesium sulphate, concentrated by evaporation and purified over silica gel with methylene chloride and then with increasing amounts of methanol (up to 10%).

Yield: 12.6 g,
Melting point: 188°–191° C.

EXAMPLE C 7,8-Dimethoxy-2,3,4,5-tetrahydro-1H-3-benzazepine

A solution of glacial acetic acid (1.8 g) in dioxan (10 ml) is added dropwise to a suspension of 7,8-dimethoxy-1,3,4,5-tetrahydro-2H-3-benzazepin-2-one (1.3 g, 6 mmol) and sodium borohydridel (1 g, 3 mmol) in dioxan (20 ml), refluxed for 3 hours, concentrated by evaporation and decomposed with water. The mixture is extracted twice with methylene chloride, the extract is concentrated by evaporation and the residue is taken up in ether. After filtration the ether is eliminated in vacuo.

Yield: 1.1 g,
Melting point: 86°–89° C.

EXAMPLE D 6,9-Dimethoxy-1,3-dihydro-2H-3-benzazepin-2-one

N-(2,2-dimethoxyethyl)-2,5-dimethoxyphenyl-acetamide (2.0 g, 0.007 mol) is covered with polyphosphoric acid (3 ml) and stirred for 60 minutes at 90° C. Then ice water is added, the precipitated product is suction filtered and dried.

Yield: 0.98 g,
Melting point: 188°–191° C.

EXAMPLE E 7,8-Dimethyl-1,3-dihydro-2H-3-benzazepin-2-one

The title compound is prepared analogously to Example D from N-(2,2-dimethoxyethyl)-3,4-dimethylphenylacetamide and polyphosphoric acid.

Melting point: 220°–224° C.

EXAMPLE F 7,8-Dimethoxy-1,3,4,5-tetrahydro-2H-3-benzazepin-2,4-dione (a)

7,8-Dimethoxy-2-amino-4-bromo-1H-3-benzazepine-hydrobromide

Here, 3,4-dimethoxy-o-phenylene-diacetonitrile (3.7 g, 0.017 mol) is suspended in glacial acetic acid (10 ml) and mixed with 30% hydrobromic acid (12 ml) in glacial acetic acid at 20° C. The mixture is stirred for 3 hours at ambient temperature, the precipitate is suction filtered, washed with glacial acetic acid and then with acetone/ether and dried.

Yield: 5.3 g,
Melting point: 210°–211° C. (decomp.).

(b)

7,8-Dimethoxy-1,3,4,5-tetrahydro-2H-3-benzazepin-2,4-dione

Here, 7,8-dimethoxy-2-amino-4-bromo-1H-3-benzazepine-hydrobromide (5.3 g, 0.014 mol) is dissolved in hot water (100 ml) at 85° C., mixed with of anhydrous sodium acetate (1.3 g) and heated to 90° C. for 1 hour. The reaction mixture is cooled, suction filtered, washed with cold water and dried.

Yield: 2.9 g,
Melting point: 235° C. (decomp.).

EXAMPLE G

N-[3-(7,8-Dimethoxy-1,3,4,5-tetrahydro-2H-3-benzazepin-2-on-3-yl)-propyl]methylamine-hydrochloride First, 1-(7,8-dimethoxy-1,3,4,5-tetrahydro-2H-3-benzazepin-2-on-3-yl)-3-chloro-propane (5.9 g, 0.020 mol) and methylamine (14 g, 0.45 mol) are heated to 130° C. for 1 hour in a sealed tube. Then, the cooled reaction product is taken up in semi-concentrated sodium hydroxide solution and extracted with methylene chloride. After the extract has been dried and concentrated, the hydrochloride is precipitated from acetone/ether with ethereal hydrochloric acid.

Yield: 5.2 g,
Melting point: 110° C. (decomp.).

EXAMPLE H 7,8-Dimethoxy-2,3-dihydro-1H-3-benzazepine

A boiling suspension of of lithium aluminium hydride (0.8 g) in absolute dioxan (100 ml) is mixed with 7,8-dimethoxy-1,3-dihydro-2H-3-benzazepin-2-one (2.2 g, 0.01 mol) and then refluxed for 3 hours. While cooling with ice water, 10% ammonium chloride solution is added and the precipitate formed is suction filtered. The fitrate is evaporated in vacuo to a volume of about 20 ml, the white precipitate obtained is suction filtered and washed with a little dioxan.

Yield: 0.9 g,
Melting point: 162°–163° C.

EXAMPLE I 1-(7,8-Dimethoxy-1,3,4,5-tetrahydro-2H-3-benzazepin-2-on-3-yl)-3-chloro-propane (a)

1-(7,8-Dimethoxy-1,3-dihydro-2H-3-benzazepin-2-on3-yl)-3-chloro-propane

Here, 7,8-dimethoxy-1,3-dihydro-2H-3-benzazepin-2-one (131.5 g, 0.6 mol) is suspended in dimethylsulfoxide (900 ml) and mixed with potassium tert.butoxide (80.8 g, 0.72 mol) with stirring. After 10 minutes, the solution obtained is added dropwise, while cooling with ice water, to 1-bromo-3-chloropropane (77 ml, 0.72 mol) in dimethylsulfoxide (300 ml). After 1 hour the mixture is poured into ice water. After a short time the greasy precipitate begins to crystalize. The precipitate is suction filtered, dissolved in acetone, precipitated with water once again, suction filtered and dried.

Yield: 155.5 g,
Melting point: 101°–103° C.

(b) 1-(7,8-Dimethoxy-1,3,4,5-tetrahydro-2H-3-benzazepin-2-on-3-yl)-3-chloro-propane Here, 1-(7,8-dimethoxy-1,3-dihydro-2H-3-benzazepin-2-on-3-yl)-3-chloro-propane (59.2 g, 0.2 mol) is hydrogenated in glacial acetic acid (500 ml) in the presence of 10% palladium/charcoal (5 g) for 6 hours at 50° C. and at 5 bar. The catalyst is suction filtered, the glacial acetic acid is distilled off in vacuo and after the addition of water, the residue is neutralized with potassium carbonate. The precipitate is suction filtered, washed with water until free from salt and dried.

Yield: 53 g,
Melting point: 85°–86° C.

EXAMPLE J 1-(7,8-Dimethoxy-1,2,4,5-tetrahydro-3H-3-benzazepin-3-yl)-3-chloro-propane Here, 1-(7,8-dimethoxy-1,3,4,5-tetrahydro-2H-3-benzazepin-2-on-3-yl)-3-chloro-propane (1.5 g, 0.005 mol) is dissolved in tetrahydrofuran (20 ml) and, after the addition of boron trifluoride etherate (0.55 ml, 0.0044 mol) and a 2 molar solution of boranedimethylsulfide in toluene (3 ml, 0.006 mol), the mixture is refluxed for 2 hours. Then, further boranedimethylsulfide solution (3 ml) is added and again the mixture is refluxed for 2 hours. After decomposition with methanol the solvents are distilled off and the residue is heated to 100° C. for 10 minutes with semi-concentrated hydrochloric acid (6 ml). The reaction product is extracted with ethyl acetate, the acidic aqueous phase is made alkaline and again extracted with ethyl acetate. The extract is dried, concentrated by evaporation and purified over an aluminium oxide column (activity stage II–III) with methylene chloride.

Yield: 0.55 g,
Melting point: 62°–64° C.

EXAMPLE K 3-(N-Methyl-2-amino-ethyl)-benzo[b]thiophene (a) Benzo[b]thienyl-3-acetic acid-N-methyl-amide Carbonyldiimidazole (2.0 g, 0.012 mol) is added in batches to a solution of benzo[b]thienyl-3-acetic acid (2.3 g, 0.012 mol) in ethylacetate (40 ml) and the mixture is stirred for 5 hours at ambient temperature. After the addition of 18% of methylamine in ethylacetate (7 ml) the mixture is stirred for a further 3 hours, then it is extracted with 1M sodium hydroxide solution, the organic phase is washed with water, dried over sodium sulphate and, after concentration by evaporation, purified by chromatography over a silica gel column.

Yield: 0.98 g,
Melting point: 123°–124° C.

(b) 3-(N-Methyl-2-amino-ethyl)-benzo[b]thiophene

Borane-dimethylsulfide (1.1 ml of a 10M solution in tetrahydrofuran) (0.85 g, 0.011 mol) is slowly added dropwise to a refluxed solution of benzo[b]thienyl-3-acetic acid-N-methyl-amide (1.9 g, 0.0093 mol) and boron trifluoride etherate (1.3 g, 0.0093 mol) of in tetrahydrofuran (40 ml) and the resulting mixture is refluxed for a further 4.5 hours. After being concentrated by evaporation it is heated to 100° C., mixed with 6M hydrochloric acid (1.6 ml) and kept at this temperature for 30 minutes. It is left to cool, 6M sodium hydroxide solution (2.3 ml) is added, the solution is saturated with potassium carbonate and extracted with ether. The extract is washed, dried, evaporated and purified over an aluminium oxide column of activity stage II.

Yield: 0.85 g,
Oil, $R_f$-value: 0.40 (aluminium oxide, methylene chloride/methanol=50:1).
Calculated: C 69.06, H 6.85, N 7.32, S 16.76, Found: 69.15, 6.63, 7.20, 16.66.

EXAMPLE L 2-(N-Methyl-2-amino-ethyl)furan (a) 2-(N-Formyl-2-amino-ethyl)-furan Here, 2-(2-amino-ethyl)furan (10.0 g, 0.090 mol) is refluxed with ethyl formate (80 ml, 1.0 mol) for 12 hours. The reaction product is concentrated by evaporation and distilled in vacuo.

Yield: 11.6 g,
Boiling point: 140° C./0.06 Torr.
Calculated: C 60.42, H 6.52, N 10.07, Found: 60.71, 6.35, 10.24.

(b) 2-(N-Methyl-2-amino-ethyl)-furan

Here, 2-(N-formyl-2-amino-ethyl)-furan (1.4 g, 0.010 mol) is added dropwise at 0°–5° C. under nitrogen to a suspension of lithium aluminium hydride (0.50 g, 0.013 mol) in ether (20 ml), stirred for 30 minutes at ambient temperature then refluxed for 7 hours. After cooling, the mixture is decomposed with dilute sodium hydroxide solution and suction filtered. The organic phase is dried, concentrated by evaporation and distilled in vacuo.

Yield: 1.0 g,
Boiling point: 110° C./12 Torr.
$R_f$ value: 0.78 (aluminium oxide, methylene chloride/methanol=9:1).

EXAMPLE M 1-(7-Bromo-8-methoxy-1,3,4,5-tetrahydro-2H-3-benzazepin-2-on-3-yl)-3-chloro-propane (a) 8-Methoxy-1,3,4,5-tetrahydro-2H-3-benzazepin-2-one Here, 8-methoxy-1,3-dihydro-2H-benzazepin-2-one (melting point: 190°–191° C.) (56.8 g, 0.3 mol), dissolved in glacial acetic acid (600 ml), is hydrogenated for 12 hours in the presence of 10% palladium/charcoal (5 g) at 80° C. and at 5 bar. The catalyst is removed by suction filtering and the acetic acid is distilled off in vacuo. The residue is mixed with water, neutralized with potassium carbonate, the precipitate obtained is suction filtered, washed with water and dried.

Yield: 51.1 g,
Melting point: 160°–161° C.

(b) 7-Bromo- and 9-bromo-8-methoxy-1,3,4,5-tetrahydro-2H-3-benzazepin-2-one

At 3°–5° C., with stirring bromine (6.4 g=2.03 ml, 0.04 mol) in glacial acetic acid (10 ml) is added dropwise to 8-methoxy-1,3,4,5-tetrahydro-2H-3-benzazepin-2-one (7.4 g, 0.04 mol) in 80% acetic acid (100 ml). After 15 minutes the mixture is poured into ice water, neutralized with potassium carbonate, the precipitate is suction filtered, washed with a little water and dried. The isomer mixture obtained is separated by chromatography over a silica gel column (eluant: ethyl acetate).

Yield: 5.7 g of the 9-bromo isomer

IR spectrum: (methylenechloride): 3400 cm$^{-1}$ (NH), 1660 cm$^{-1}$ (C=O)

4.1 g of the 7-bromo isomer

IR spectrum (calcium bromide): 3220 cm$^{-1}$ (NH), 1665 cm$^{-1}$ (CO)

(c)
1-(7-Bromo-8-methoxy-1,3,4,5-tetrahydro-2H-3-benzazepin-2-on-3-yl)-3-chloro-propane A 55% sodium hydride dispersion (0.24 g, 5.5 mmol) in oil is added to 7-bromo-8-methoxy-1,3,4,5-tetrahydro-2H-3-benzazepin-2-one (1.35 g, 5 mmol) in dimethylsulfoxide (15 ml) and the mixture is stirred for half an hour at ambient temperature and for 10 minutes at 35°–40° C. The solution is added dropwise, with stirring, to 1-bromo-3-chloro-propane (0.79 g, 5.5 mmol) in dimethylsulfoxide (5 ml). Then the mixture is stirred for 2 hours at ambient temperature, poured into ice water and extracted (4 times) with methylene chloride. The methylene chloride extracts are washed several times with water, dried and evaporated in vacuo. The residue is purified over a silica gel column with ethyl acetate as eluant.

Yield: 210 mg,
Melting point: 119°–120° C.

EXAMPLE N 1-(7-Methoxy-1,3,4,5-tetrahydro-2H-3-benzazepin-2-on-3-yl)-3-chloro-propane (a)
7-Methoxy-1,3,4,5-tetrahydro-2H-3-benzazepin-2-one N-chloroacetyl-N-(2-(3-methoxy-phenyl)-ethyl)-amine (3.1 g, 0.0136 mol) is dissolved in ethanol (270 ml) and water (1530 ml) and illuminated for 10 hours with a high pressure mercury lamp under a nitrogen atmosphere at 20°–25° C. The solution is evaporated down (to a volume of about 400 ml), mixed with sodium bicarbonate and extracted several times with ethyl acetate. The extracts are dried over magnesium sulphate, concentrated by evaporation and the residue is purified over a silica gel column with ethyl acetate as eluant.

Yield: 820 mg,
Melting point: 152°–154° C.

(b)
1-(7-Methoxy-1,3,4,5-tetrahydro-2H-3-benzazepin-2-on-3-yl)-3-chloro-propane

Here, 7-methoxy-1,3,4,5-tetrahydro-2H-3-benzazepin-2-one (1.15 g, 6 mmol) is dissolved in absolute tetramethylurea (30 ml), mixed with 55% sodium hydride dispersion (in oil) (300 mg) and stirred for 2 hours at 20°–25° C. under a nitrogen atmosphere. The reaction mixture obtained is added dropwise, with stirring at 15°–20° C., under a nitrogen atmosphere, to 1-chloro-3-iodopropane (1.6 g, 7.8 mmol) dissolved in tetramethylurea (20 ml) and then stirred for 3 hours at ambient temperature. Ethyl acetate (300 ml) is then added and the mixture is extracted (6 times) with water. The organic solution is dried over magnesium sulphate, concentrated by evaporation and the residue is purified over a silica gel column with methylene chloride and increasing amounts of ethanol (up to 2%).

Yield: 410 mg,
IR spectrum (methylene chloride): 1650 cm$^{-1}$ (CO).

EXAMPLE O 1-(7-Nitro-8-methoxy-1,3,4,5-tetrahydro-2H-3-benzazepin-2-on-3-yl)-3-chloro-propane Here, 1-(8-methoxy-1,3,4,5-tetrahydro-2H-3-benzazepin-2-on-3-yl)3chloro-propane (28.5 g, 0.016 mol) is stirred into concentrated nitric acid (350 ml) for half an hour at 20°–25° C. The solution is poured onto ice water, neutralized with potassium carbonate and extracted twice with methylene chloride. The extract is dried over magnesium sulphate, concentrated by evaporation in vacuo and the residue is purified over a silica gel column with ethyl acetate as eluant.

Yield: 11 g,
Melting point: 127°–128° C.

EXAMPLE P 1-(1,3,4,5-Tetrahydro-2H-3-benzazepin-2,4-dion-3-yl)-3-chloro-propane (a) 2-Amino-4-bromo-1H-3-benzazepine-hydrobromide This compound is prepared from o-phenylenediacetonitrile (5.0 g, 0.032 mol) analogously to Example F(a).

Yield: 8.0 g (b) 1,3,4,5-Tetrahydro-2H-3-benzazepin-2,4-dione

This compound is prepared from 2-amino-4-bromo-1H-3-benzazepine-hydrobromide (8.0 g, 0.025 mol) analogously to Example F(b).

Yield: 3.7 g,
Melting point: 189°–191° C.

(c)
1-(1,3,4,5-Tetrahydro-2H-3-benzazepin-2,4-dion-3-yl)-3-chloro-propane

Here, 1,3,4,5-tetrahydro-2H-3-benzazepin-2,4-dione (3.5 g, 0.020 mol) is suspended in dimethylformamide (30 ml) and potassium tert. butoxide (2.5 g) is added with stirring. After 10 minutes the resulting solution is added dropwise, while cooling with ice, to 1-bromo-3-chloro-propane (3.5 ml) in dimethylformamide (20 ml). After one hour it is poured onto ice water. After a short time the greasy precipitate crystallizes. The precipitate is suction filtered, dissolved in acetone, reprecipitated with water, suction filtered and dried.

Yield: 4.7 g.

EXAMPLE Q 3-(7,8-Dimethoxy-1,3-dihydro-2H-3-benzazepin-2-on-3-yl)-propionaldehyde (a)
3-(7,8-Dimethoxy-1,3-dihydro-2H-3-benzazepin-2-on-3-yl)-propionaldehyde diethylacetal This compound is prepared analogously to Example I(a) by reacting 7,8-dimethoxy-1,3-dihydro-2H-3-benzazepin-2-one with 3-chloro-propionaldehyde diethylacetal.

(b)
3-(7,8-Dimethoxy-1,3-dihydro-2H-3-benzazepin-2-on-3-yl)-propionaldehyde

Here, 3-(7,8-dimethoxy-1,3-dihydro-2H-3-benzazepin-2-on-3-yl)-propionaldehyde diethylacetal (3.5 g, 0.01 mol) is heated to 40° C. for 2 hours in 2N sulphuric acid (50 ml) and ethanol (50 ml). The alcohol is distilled off in vacuo, the residue is made alkaline with saturated potassium carbonate solution while cooling and extracted several times with ethyl acetate. The ethyl acetate extract is extracted twice with 5% sodium hydrogen sulfate solution. The bisulphate extract is acidified with concentrated hydrochloric acid and heated to 40° C. in vacuo for half an hour to eliminate the sulphur dioxide. Then saturated potassium carbonate solution is added, the mixture is extracted several times with methylene chloride, dried over magnesium sulphate and concentrated by evaporation.

Melting point: 95°–96° C.

Yield: 1.7 g.

Preparation of the end products:

EXAMPLE 1

1-(7,8-Dimethoxy-1,3,4,5-tetrahydro-2H-3-benzazepin-2-on-3-yl)-3-[N-methyl-N-(2-(6-methoxy-benzo[b]thienyl-3)-ethyl)-amino]propane-dihydrochoride First, 1-(7,8-dimethoxy-1,3,4,5-tetrahydro-2H-3-benzazepin-2-on-3-yl)-3-chloro-propane (0.80 g, 0.0027 mol) and 3-(N-methyl-2-amino-ethyl)-6-methoxy-benzo[b]-thiophene (0.60 g, 0.0027 mol) are heated to 60° C. for 30 minutes in triethylamine (5 ml). The temperature is then increased to reflux temperature and maintained for 3 hours. After the triethylamine has been distilled off the mixture is heated to 100° C. for a further 5 hours. The product obtained is purified over a silica gel column with methylene chloride/methanol=25:1 as eluant, taken up in methanol and precipitated with ethereal hydrochloride acid in the form of the hydrochloride.

Yield: 0.69 g

Calculated: C 58.36, H 6.53, N 5.04, Cl 12.76, S 5.77, Found: 58.43, 6.83, 4.71, 12.86, 5.65.

$R_f$ value of the free base: 0.48 (Silica gel, methylene chloride/methanol=9:1).

EXAMPLE 2

1-(7,8-Dimethoxy-1,3,4,5-tetrahydro-2H-3-benzazepin-2-on-3-yl)-3-[N-methyl-N-(4-(imidazolyl-1)-butyl)-amino]-propane Here, 1-(7,8-dimethoxy-1,3,4,5-tetrahydro-2H-3-benzazepin-2-on-3-yl)-3-(n-methyl-amino)-propane-hydrochloric (1.65 g, 0.0050 mol) is refluxed for 2 hours with 4-(imidoazolyl-1)-1-chlorobutane (0.80 g, 0.0050 mol) and anhydrous potassium carbonate (2.6 g, 0.020 mol) in dimethylformamide. The solvent is distilled off, the residue is taken up in semi-concentrated sodium hydroxide solution and extracted with chloroform. The extract is washed with saline solution, dried with sodium sulphate, concentrated by evaporation and purified over a aluminium oxide column (activity state II eluant: methylene chloride).

Yield: 0.91 g, $R_f$ value: 0.53 (Silica gel, methylene chloride/methanol=9:1).

EXAMPLE 3

1-(7,8-Dimethoxy-1,3,4,5-tetrahydro-2H-3-benzazepin-2,4-dion-3-yl)-3-[N-methyl-N-(2-(pyridyl-4)-ethyl)-amino]propane-dihydrochloride-monohydrate First, 7,8-dimethoxy-1,3,4,5-tetrahydro-2H-3-benzazepin-2,4-dione (1.55 g, 0.0066 mol) is dissolved in dimethylformamide (40 ml) with gentle heating. After cooling to 0° C., potassium tert.butoxide (0.9 g, 0.008 mol) is added, the mixture is stirred for a further 5 minutes and then mixed with 3-[N-methyl-N-(2-pyridyl-4)-ethyl)amino]-1-bromo-propane (1.7 g, 0.006 mol). The mixture is stirred overnight at ambient temperature, the solvent is removed by centrifuging and the residue is purified over a silica gel column (elution with methylene chloride/ethanol). The purified base is taken up in methanol and the hydrochloride is precipitated with ethereal hydrchloric acid.

Yield: 0.75 g,

Calculated: C 54.97, H 6.62, N 8.36, Cl 14.11, Found: 55.20, 6.82, 8.17, 13.82.

$R_f$ value of the free base: 0.25 (silica gel, methylene chloride/ethanol=9:1).

EXAMPLE 4

1-(7,8-Dimethoxy-1,3,4,5-tetrahydro-2H-3-benzazepin-2-thion-3-yl)-3-[N-methyl-N-(3-(furyl-2)-propyl)amino]propane Here, 1-(7,8-dimethoxy-1,3,4,5-tetrahydro-2H-3-benzazepin-2-on-3-yl)-3-[N-methyl-N-(3-(furyl-2)-propyl)-amino]propane (0.80 g, 0.0020 mol) and 2,4-bis-(4-methoxy-phenyl)-1,3-dithia-2,4-diphosphetane-2,4-disulphide (0.40 g, 0,0010 mol) are suspended in toluene (10 ml) and refluxed for 3 hours. The mixture is then centrifuged and then purified over a silica gel column with methylene chloride and increasing amounts of methanol.

Yield: 0.26 g,

Calculated: C 66.31, H 7.74, N 6.73, S 7.70, Found: 66.13, 7.72, 6.14, 7.71.

$R_f$ Value: 0.58 (Silica gel, methylene chloride/methanol=9:1).

EXAMPLE 5

1-(7,8-Dimethoxy-2,3-dihydro-1H-3-benzazepin-3-yl)-3-[N-methyl-N-(2-(furyl-2)-ethyl)-amino]propane A solution of 1-(7,8-dimethoxy-1,3-dihydro-2-H-3-benzazepin-2-on-3-yl)-3-[N-methyl-N-(2-(furyl-2)-ethyl)-amino]propane (0.77 g, 0.0020 mol) in absolute dioxan (5 ml) is added dropwise to a boiling suspension of lithium aluminium hydride (0.2 g, 0.005 mol) in absolute dioxan (20 ml) and kept at reflux temperature for 2 hours. The mixture is then decomposed with sodium hydroxide solution, suction filtered and purified over a silica gel column.

Yield: 0.50 g,

Calculated: C 71.32, H 8.16, N 7.56, Found: 70.90, 7.88, 7.35.

$R_f$ value: 0.70 (silica gel, methylene chloride/methanol=9:1).

EXAMPLE 6

1-(7,8-Dimethoxy-1,3,4,5-tetrahydro-2H-3-benzazepin-2-on-3-yl)-3-[N-methyl-N-(3-(thienyl-2)-propyl)-amino]-propane-hydrochloride The title compound is prepared analogously to Example 1 by reacting 1-(7,8-dimethoxy-1,3,4,5-tetrahydro-2H-3-benzazepin-2-on-3-yl)-3-chloro-propane with 2-(3-methylamino-propyl)-thiophene and subsequently precipitating the hydrochloride with ethereal hydrochloric acid.

$R_f$ value of the free base: 0.40 (silica gel, methylene chloride/methanol=9:1).

EXAMPLE 7

1-(7,8-Dimethoxy-1,3,4,5-tetrahydro-2H-3-benzazepin-2-on-3-yl)-3-[N-methyl-N-(2-(furyl-2)-ethyl)-amino]-propane The title compound is prepared analogously to Example 1 by reacting 1-(7,8-dimethoxy-1,3,4,5-tetrahydro-2H-3-benzazepin-2-on-3-yl)-3-chloro-propane with 2-(2-methylamino-ethyl)-furan.

Calculated: C 68.37, H 7.82, N 7.25 Found: 67.45, 7.73, 6.33.

$R_f$ value: 0.44 (silica gel, methylene chloride/methanol=9:1).

EXAMPLE 8

1-(7,8-Dimethoxy-1,3,4,5-tetrahydro-2H-3-benzazepin-2-on-3-yl)-3-[N-methyl-N-(3-(furyl-2)-propyl)-amino]-propane The title compound is prepared analogously to Example 1 by reacting 1-(7,8-dimethoxy-1,3,4,5-tetrahydro-2H-3-benzazepin-2-on-3-yl)-3chloro-propane with 2-(3-methylamino-propyl)-furan.

Calculated: C 68.97, H 8.05, N 6.99, Found: 68.76, 7.99, 6.78.

$R_f$ value: 0.44 (silica gel, methylene chloride/methanol=9:1).

EXAMPLE 9

1-(7,8-Dimethoxy-1,3,4,5-tetrahydro-2H-3-benzazepin-2-on-3-yl)-3-[N-methyl-N-(2-(thienyl-2)-ethyl)-amino]-propane-dihydrochloride The title compound is prepared analogously to Example 1 by reacting 1-(7,8-dimethoxy-1,3,4,5-tetrahydro-2H-3-benzazepin-2-on-3-yl)-3-chloro-propane with 2-(N-methyl-2-amino-ethyl)-thiophene and subsequently precipitating the hydrochloride with ethereal hydrochloric acid.

Melting point: 215° C. (decomp.).

EXAMPLE 10

1-(7,8-Dimethoxy-1,3,4,5-tetrahydro-2H-3-benzazepin-2-on-3-yl)-3-[N-methyl-N-(2-(thienyl-3)-ethyl)-amino]-propane-dihydrochloride The title compound is prepared analogously to Example 1 by reacting 1-(7,8-dimethoxy-1,3,4,5-tetrahydro-2H-3-benzazepin-2-on-3-yl)-3-chloro-propane with 3-(N-methyl-2-amino-ethyl)-thiophene and subsequently precipitating the hydrochloride with ethereal hydrochloric acid.

Melting point: 185° C. (decomp.).

EXAMPLE 11

1-(7,8-Dimethoxy-1,3,4,5-tetrahydro-2H-3-benzazepin-2-on-3-yl)-3-[N-methyl-N-(2-(imidazolyl-4(5)-ethyl)-amino]propane The title compound is prepared analogously to Example 1 by reacting 1-(7,8-dimethoxy-1,3,4,5-tetrahydro-2H-3-benzazepin-2-on-3-yl)-3-chloro-propane with 4-(N-methyl-2-amino-ethyl)-imidazole.

$R_f$ value: 0.60 (aluminium oxide, methylene chloride/methanol=10:1).

EXAMPLE 12

1-(7,8-Dimethoxy-1,3,4,5-tetrahydro-2H-3-benzazepin-2-on-3-yl)-3-[N-methyl-N-(2-(5,6-dimethoxy-benzo[b]-thienyl-3)-ethyl)-amino]propane The title compound is prepared analogously to Example 1 by reacting 1-(7,8-dimethoxy-1,3,4,5-tetrahydro-2H-3-benzazepin-2-on-3-yl)-3-chloro-propane with 3-(2-methylamino-ethyl)-5,6-dimethoxy-benzo[b]thiophene.

Calculated: C 65.60, H 7.08, N 54.6, Found: 65.31, 6.89, 5.72.

$R_f$ value: 0.27 (silica gel, methylene chloride/methanol=9:1).

EXAMPLE 13

1-(7,8-Dimethoxy-1,3,4,5-tetrahydro-2H-3-benzazepin-2-on-3-yl)-3-[N-methyl-N-(2-(imidazo[1,2-a]pyridyl-3)-ethyl)-amino]propane hydrochloride The title compound is prepared analogously to Example 1 by reacting 1-(7,8-dimethoxy-1,3,4,5-tetrahydro-2H-3-benzazepin-2-on-3-yl)-3-(N-methyl-amino)-propane with 2-(imidazo-[1,2-a]pyridyl-3)-ethyl chloride and subsequently precipitating the hydrochloride with ethereal hydrochloric acid.

Melting point: 130° C. (decomp.).

EXAMPLE 14

1-(7,8-Dimethoxy-1,3,4,5-tetrahydro-2H-3-benzazepin-2-on-3-yl)-3-[N-methyl-N-(2-(benzo[b]thienyl-3)-ethyl)-amino]propane hydrochloride The title compound is prepared analogously to Example 1 by reacting 1-(7,8-dimethoxy-1,3,4,5-tetrahydro-2H-3-benzazepin-2-on-3-yl)-3-chloro-propane with 3-(N-methyl-2-amino-ethyl)-benzo[b]thiophene and subsequently precipitating the hydrochloride with ethereal hydrochloric acid.

Yield: 65% of theory,
Melting point: 195° C. (decomp.).

EXAMPLE 15

1-(7,8-Dimethoxy-1,3,4,5-tetrahydro-2H-3-benzazepin-2-on-3-yl)-3-[N-methyl-N-(4-(thienyl-2)-butyl)-amino]-propane-dihydrochloride The title compound is prepared analogously to Example 1 by reacting 1-(7,8-dimethoxy-1,3,4,5-tetrahydro-2H-3-benzazepin-2-on-3-yl)-3-chloro-propane with 2-(N-methyl-4-amino-butyl)-thiophene and subsequently precipitating the hydrochloride with ethereal hydrochloric acid.

Calculated: C 57.25, H 7.21, N 5.56, Cl 14.08, S 6.37, Found: 57.60, 7.55, 5.41, 13.82, 6.43.

$R_f$ value of the free base: 0.55 (silica gel, methylene chloride/methanol=9:1).

EXAMPLE 16

1-(7,8-Dimethoxy-1,3,4,5-tetrahydro-2H-3-benzazepin-2-on-3-yl)-3-[N-methyl-N-(2-(imidazolyl-1)-ethyl)-amino]propane The title compound is prepared analogously to Example 1 by reacting 1-(7,8-dimethoxy-1,3,4,5-tetrahydro-2H-3-benzazepin-2-on-3-yl)-3chloro-propane with 1-(N-methyl-2-amino-ethyl)-imidazole.

$R_f$ value: 0.55 (aluminium oxide, methylene chloride/methanol=20:1).

EXAMPLE 17

1-(7,8-Dimethoxy-1,3,4,5-tetrahydro-2H-3-benzazepin-2-on-3-yl)-3-[N-methyl-N-(2-(1-methyl-imidazolyl-4)-ethyl)-amino]propane The title compound is prepared analogously to Example 1 by reacting 1-(7,8-dimethoxy-1,3,4,5-tetrahydro-2H-3-benzazepin-2-on-3-yl)-3-chloro-propane with 1-methyl-4-(N-methyl-2-amino-ethyl)-imidazole.

$R_f$ value: 0.70 (aluminium oxide, methylene chloride/methanol=20:1).

EXAMPLE 18

1-(7,8-Dimethoxy-1,3,4,5-tetrahydro-2H-3-benzazepin-2-on-3-yl)-3-[N-methyl-N-(2-(benzo[b]thienyl-3)-1-methyl-ethyl)-amino]propane-hydrochloride The tile compound is prepared analogously to Example 1 by reacting 1-(7,8-dimethoxy-1,3,4,5-tetrahydro-2H-3-benzazepin-2-on-3-yl)-3-chloro-propane with 3-(N-methyl-2-amino-propyl)-benzo[b]thiophene and subsequently precipitating the hydrochloride with ethereal hydrochloric acid.

$R_f$ value of the free base: 0.65 (silica gel, methylene chloride/methanol=5:1).

EXAMPLE 19

1-(7,8-Dimethoxy-1,3,-dihydro-2H-3-benzazepin-2-on-3-yl)-3-[N-methyl-N-(2-(furyl-2)-ethyl)-amino]propane hydrochloride The title compound is prepared analogously to Example 1 by reacting 1-(7,8-dimethoxy-1,3-dihydro-2H-3-benzazepin-2-on-3-yl)-3-chloro-propane with 2-(2-methylamino-ethyl)-furan and subsequently precipitating the hydrochloride with ethereal hydrochloric acid.

Calculated: C 62.77, H 6.94, N 6.66, Cl 8.42, Found: 62.80, 7.19, 6.49, 8.32.

$R_f$ value of the free base: 0.57 (silica gel, methylene chloride/methanol=9:1).

EXAMPLE 20

1-(7,8-Dimethoxy-1,3,4,5-tetrahydro-2H-3-benzazepin-2-on-3-yl)-3-[N-methyl-N-(2-(1H-benzo[d]imidazolyl-1)-ethyl)-amino]propane The title compound is prepared analogously to Example 1 by reacting 1-(7,8-dimethoxy-1,3,4,5-tetrahydro-2H-3-benzazepin-2-on-3-yl)-3-chloro-propane with 1-(2-methylamino-ethyl)-1H-benzo[d]imidazole.

Calculated: C 68.78, H 7.39, N 12.83, Found: 68.50, 7.39, 12.57.

$R_f$ value: 0.57 (silica gel, methylene chloride/methanol=9:1).

EXAMPLE 21

1-(7,8-Dimethoxy-1,3,4,5-tetrahydro-2H-3-benzazepin-2-on-3-yl)-3-[N-methyl-N-(2-(2-benzyl-1H-benzo[d]imidazolyl-1)-ethyl)-amino]propane The title compound is prepared analogously to Example 1 by reacting 1-(7,8-dimethoxy-1,3,4,5-tetrahydro-2H-3-benzazepin-2-on-3-yl)-3-chloro-propane with 1-(2-methylamino-ethyl)-2-benzyl-1H-benzo[d]imidazole.

$R_f$ value: 0.49 (silica gel, methylene chloride/methanol=9:1).

EXAMPLE 22

1-(7,8-Dimethoxy-1,3,4,5-tetrahydro-2H-3-benzazepin-2-on-3-yl)-3-[N-methyl-N-(2-(4-methyl-thiazolyl-5)-ethyl)-amino]propane dihydrochloride The title compound is prepared analogously to Example 1 by reacting 1-(7,8-dimethoxy-1,3,4,5-tetrahydro-2H-3-benzazepin-2-on-3-yl)-3-chloro-propane with 4-methyl-5-(N-methyl-2-amino-ethyl)-thiazole and subsequently precipitating the hydrochloride with ethereal hydrochloric acid.

Melting point: 196°-197.5° C. (decomp.).

EXAMPLE 23

1-(7,8-Dimethoxy-1,3,4,5-tetrahydro-2H-3-benzazepin-2-on-3-yl)-3-[N-methyl-N-(2-(1-methyl-pyrrolyl-2)-ethyl)-amino]propane The title compound is prepared analogously to Example 1 by reacting 1-(7,8-dimethoxy-1,3,4,5-tetrahydro-2H-3-benzazepin-2-on-3-yl)-3-chloro-propane with 1-methyl-2-(N-methyl-2-amino-ethyl)-pyrrole.

Calculated: C 69.14, H 8.33, N 10.52, Found: 70.01, 8.24, 10.76.

$R_f$ value: 0.76 (aluminium oxide N, methylene chloride/ethanol=19:1).

EXAMPLE 24

1-(7,8-Dimethoxy-1,3,4,5-tetrahydro-2H-3-benzazepin-2-on-3-yl)-3-[N-methyl-N-(picolyl-2)-amino]propane dihydrochloride The title compound prepared analogously to Example 1 by reacting 1-(7,8-dimethoxy-1,3,4,5-tetrahydro-2H-3-benzazepin-2-on-3-yl)-3-chloro-propane with N-(picolyl-2)-methylamine and subsequently precipitating the hydrochloride with ethereal hydrochloric acid.

$R_f$ value of the free base: 0.50 (silica gel, methylene chloride/ethanol=4:1).

EXAMPLE 25

1-(7,8-Dimethoxy-1,3,4,5-tetrahydro-2-H-3-benzazepin-2-on-3-yl)-3-[N-methyl-N-(picolyl-3)-amino]propane dihydrochloride The title compound prepared analogously to Example 1 by reacting 1-(7,8-dimethoxy-1,3,4,5-tetrahydro-2H-3-benzazepin-2-on-3-yl)-3-chloro-propane with N-(picolyl-3)-methylamine and subsequently precipitating the hydrochloride with ethereal hydrochloric acid.

Melting point: 176°-178° C.

EXAMPLE 26

1-(7,8-Dimethoxy-1,3,4,5-tetrahydro-2H-3-benzazepin-2-on-3-yl)-3-[N-methyl-N-(2-(pyridyl-4)-ethyl)-amino]propane dihydrochloride The title compound prepared analogously to Example 1 by reacting 1-(7,8-dimethoxy-1,3,4,5-tetrahydro-2H-3-benzazepin-2-on-3-yl)-3-chloro-propane with 4-(2-methylamino-ethyl)-pyridine and subsequently precipitating the hydrochloride with ethereal hydrochloric acid.

Melting point: 116°-118° C.

EXAMPLE 27

1-(7,8-Dimethoxy-1,3,4,5-tetrahydro-2H-3-benzazepin-2-on-3-yl)-3-[N-methyl-N-(2-(pyridyl-2)-ethyl)-amino]-propane dihydrochloride The title compound prepared analogously to Example 1 by reacting 1-(7,8-dimethoxy-1,3,4,5-tetrahydro-2H-3-benzazepin-2-on-3-yl)-3-chloro-propane with 2-(2-methylamino-ethyl)-pyridine and subsequently precipitating the hydrochloride with ethereal hydrochloric acid.

Melting point: 165°–167° C.

EXAMPLE 28

1-(7,8-Dimethoxy-1,3,4,5-tetrahydro-2H-3-benzazepin-2-on-3-yl)-3-[N-methyl-N-(2-(6,7-dimethoxy-isoquinolyl-4)-ethyl)-amino]propane dihydrochloride monohydrate The title compound prepared analogously to Example 1 by reacting 1-(7,8-dimethoxy-1,3,4,5-tetrahydro-2H-3-benzazepin-2-on-3-yl)-3-chloro-propane with 6,7-dimethoxy-4-(2-methylamino-ethyl)-isoquinoline and subsequently precipitating the hydrochloride with ethereal hydrochloric acid.

Calculated: C 58.18, H 6.56, N 7.02, Cl 11.84, Found: 57.75, 7.19, 7.28, 12.03.

$R_f$ value of the free base: 0.760 (silica gel, ethyl acetate/ethanol/ammonia=50:45:5).

EXAMPLE 29

1-(7,8-Dimethoxy-1,3,4,5-tetrahydro-2H-3-benzazepin-2-on-3-yl)-3-[N-methyl-N-(2-(pyridyl-3)-ethyl)-amino]-propane dihydrochloride hemihydrate The title compound prepared analogously to Example 1 by reacting 1-(7,8-dimethoxy-1,3,4,5-tetrahydro-2H-3-benzazepin-2-on-3-yl)-3-chloro-propane with 3-(2-methylamino-ethyl)-pyridine and subsequently precipitating the hydrochloride with ethereal hydrochloric acid.

Melting point: 110°–112° C.

Calculated: C 57.62, H 7.14, N 8.76, Cl 14.79, Found: 57.23, 7.34, 8.67, 14.52.

EXAMPLE 30

1-(7,8-Dimethoxy-1,2,4,5-tetrahydro-3H-3-benzazepin-3-yl)-3-[N-methyl-N-(2-(pyridyl-4)-ethyl)-amino]propane trihydrochloride The title compound prepared analogously to Example 1 by reacting 1-(7,8-dimethoxy-1,2,4,5-tetrahydro-3H-3-benzazepin-3-yl)3-chloro-propane with 4-(2-methylamino-ethyl)-pyridine and subsequently precipitating the hydrochloride with ethereal hydrochloric acid.

Melting point: 257°–259° C.

Calculated: C 56.04, H 7.36, N 8.52, Cl 21.58, Found: 55.82, 7.31, 8.52, 21.53.

EXAMPLE 31

1-(7,8-Dimethoxy-1,3,4,5-tetrahydro-2H-3-benzazepin-2-on-3-yl)-3-[N-methyl-N-(2-(pyridyl-4)-ethyl)-amino]-propane dihydrochloride Here, 3-(7,8-dimethoxy-1,3-dihydro-2H-3-benzazepin-2-on-3-yl)-propionaldehyde (1.1 g, 0.0040 mol) is hydrogenated in ethanol (30 ml) in the presence of 4-(2-methylamino-ethyl)pyridine (0.60 g, 0.0044 mol) and 10% palladium/charcoal (0.2 g) at 50° C. for 20 hours at 5 bar. The catalyst is removed by suction filtering, the residue is concentrated by evaporation, purified over an aluminium oxide column of activity stage II-III with methylene chloride/ethanol as eluant and the hydrochloride is precipitated with ethereal hydrochloric acid.

Yield: 0.98 g,

Melting point: 116°–118° C.

EXAMPLE 32

1-(7,8-Dimethoxy-1,3,4,5-tetrahydro-2H-3-benzazepin-2-on-3-yl)-3-[N-methyl-N-(2-(benzo[b]furyl-3)-ethyl)-amino]propane Here, 1-(7,8-dimethoxy-1,3,4,5-tetrahydro-2H-3-benzazepin-2-on-3-yl)-3-chloro-propane (1.5 g, 0.005 mol) is refluxed for 4 hours with 3-(N-methyl-2-amino-ethyl)-benzo[b]furan (0.88 g, 0.005 mol) and anhydrous potassium carbonate (7 g) in dimethylformamide (50 ml). The solvent is distilled off, the residue is taken up in semi-concentrated sodium hydroxide solution and extracted with chloroform. The extract is washed with saline solution, dried with sodium sulphate, concentrated by evaporation and purified over a silica gel column (eluant: methylene chloride/methanol=20:1 to 5:1).

Yield: 0.2 g,

Calculated: C 71.53, H 7.39, N 6.42, Found: 71.43, 7.21, 6.22.

$R_f$ value: 0.35 (silica gel, methylene chloride/methanol=9:1)

EXAMPLE 33

1-(7,8-Dimethoxy-1,3-dihydro-2H-3-benzazepin-2-on-3-yl)-3-[N-methyl-N-(2-benzo[b]thienyl-3)-ethyl)-amino]-propane hydrochloride The title compound is prepared analogously to Example 32 by reacting 1-(7,8-dimethoxy-1,3-dihydro-2H-3-benzazepin-2-on-3-yl)-3-chloro-propane with 3-(N-methyl-2-amino-ethyl)-benzo[b]thiophene and subsequently precipitating the hydrochloride with ethereal hydrochloric acid.

Calculated: C 64.12, H 6.42, N 5.75, S 6.58, Cl 7.28, Found: 63.93, 6.71, 5.70, 6.32, 7.39.

$R_f$ value of the free base: 0.55 (silica gel, methylene chloride/methanol=9:1).

EXAMPLE 34

1-(7,8-Dimethoxy-1,3,4,5-tetrahydro-2H-3-benzazepin-2-on-3-yl)-3-[N-methyl-N-(3-(benzo[b]thienyl-3)-propyl)-amino]propane hydrochloride The title compound is prepared analogously to Example 32 by reacting 1-(7,8-dimethoxy-1,3,4,5-tetrahydro-2H-3-benzazepin-2-on-3-yl)-3-chloro-propane with 3-(3-methylamino-propyl)-benzo[b]thiophene and subsequently precipitating the hydrochloride with ethereal hydrochloric acid.

Calculated: C 64.46, H 7.01, N 5.57, S 6.37, Cl 7.05, Found: 64.32, 7.00, 5.47, 6.61, 7.12.

$R_f$ value of the free base: 0.30 (silica gel, methylene chloride/methanol=9:1).

EXAMPLE 35

1-(7,8-Dimethoxy-1,3,4,5-tetrahydro-2H-3-benzazepin-2-on-3-yl)-3-[N-methyl-N-((benzo[b]thienyl-3)-methyl)-amino]propane dihydrochloride The title compound is prepared analogously to Example 2 by reacting 1-(7,8-dimethoxy-1,3,4,5-tetrahydro-2H-3-benzazepin-2-on-3-yl)-3-(N-methyl-amino)-propane with 3-chloromethyl-benzo[b]thiophene and subsequently precipitating the dihydrochloride with ethereal hydrochloric acid.

Melting point: 218°–220° C.

Calculated: C 58.70, H 6.31, N 5.48, S 6.27, Cl 13.86, Found: 58.68, 6.25, 5.25, 6.71, 13.62.

EXAMPLE 36

1-(7,8-Dimethoxy-1,3,4,5-tetrahydro-2H-3-benzazepin-2-on-3-yl)-3-[N-methyl-N-(2-(5-methyl-benzo[b]thienyl-3)-ethyl)-amino]propane dihydrochloride The title compound is prepared analogously to Example 1 by reacting 1-(7,8-dimethoxy-1,3,4,5-tetrahydro-2H-3-benzazepin-2-on-3-yl)-3-chloro-propane with 3-(N-methyl-2-amino-ethyl)-5-methyl-benzo[b]thiophene and subsequently precipitating the dihydrochloride with ethereal hydrochloric acid.

Calculated: C 60.10, H 6.73, N 5.19, S 5.94, Cl 13.14, Found: 60.08, 6.57, 5.15, 6.36, 13.46.

$R_f$ value of the free base: 0.40 (silica gel, methylene chloride/methanol=9:1).

EXAMPLE 37

1-(7,8-Dimethoxy-1,3,4,5-tetrahydro-2H-3-benzazepin-2-on-3-yl)-3-[N-methyl-N-(2-(6-methoxy-benzo[b]furyl-3)-ethyl)-amino]propane hydrochloride The title compound is prepared analogously to Example 1 by reacting 1-(7,8-dimethoxy-1,3,4,5-tetrahydro-2H-3-benzazepin-2-on-3-yl)-3-chloro-propane with 3-(2-methylamino-ethyl)-6-methoxy-benzo[b]furan and subsequently precipitating the hydrochloride with ethereal hydrochloric acid.

Calculated: C 64.47, H 7.01, Cl 7.05, N 5.57, Found: 64.52, 6.99, 7.20, 5.37.

$R_f$ value of the free base: 0.35 (silica gel, methylene chloride/methanol=10:1).

EXAMPLE 38

1-(7,8-Dimethoxy-1,3,4,5-tetrahydro-2H-3-benzazepin-2-on-3-yl)-3-[N-methyl-N-(2-(4-methoxy-benzo[b]thienyl-3)-ethyl)-amino]propane hydrochloride The title compound is prepared analogously to Example 1 by reacting 1-(7,8-dimethoxy-1,3,4,5-tetrahydro-2H-3-benzazepin-2-on-3-yl)-3-chloro-propane with 3-(2-methylamino-ethyl)-4-methoxy-benzo[b]thiophene and subsequently precipitating the hydrochloride with ethereal hydrochloric acid.

Calculated: C 62.47, H 6.80, Cl 6.83, N 5.40, Found: 62.36, 6.94, 6.44, 5.51.

$R_f$ value of the free base: 0.41 (silica gel, methylene chloride/methanol=9:1).

EXAMPLE 39

1-(7,8-Dimethoxy-1,3,4,5-tetrahydro-2H-3-benzazepin-2-on-3-yl)-3-[N-methyl-N-(2-(5-bromo-benzo[b]thienyl-3)-ethyl)-amino]propane The title compound is prepared analogously to Example 1 by reacting 1-(7,8-dimethoxy-1,3,4,5-tetrahydro-2H-3-benzazepin-2-on-3-yl)-3-chloro-propane with 3-(2-methylamino-ethyl)-5-bromo-benzo[b]thiophene.

Calculated: C 58.75, H 5.88, N 5.27, S 6.03, Found: 58.63, 5.63, 5.03, 6.20.

$R_f$ value: 0.50 (silica gel, methylene chloride/methanol=9:1).

EXAMPLE 40

1-(7,8-Dimethoxy-1,3,4,5-tetrahydro-2H-3-benzazepin-2-on-3-yl)-3-[N-methyl-N-(2-(benzo[b]furyl-2)-ethyl)-amino]propane dihydrochloride The title compound is prepared analogously to Example 1 by reacting 1-(7,8-dimethoxy-1,3,4,5-tetrahydro-2H-3-benzazepin-2-on-3-yl)-3-chloro-propane with 2-(2-methylamino-ethyl)-benzo[b]furan and subsequently precipitating the dihydrochloride with ethereal hydrochloric acid.

Calculated: C 61.30, H 6.53, C 13.92, N 5.50, Found: 61.33, 6.63, 13.53, 5.66.

$R_f$ value of the free base: 0.42 (silica gel, methylene chloride/methanol=10:1).

EXAMPLE 41

1-(7,8-Dimethoxy-1,3,4,5-tetrahydro-2H-3-benzazepin-2-on-3-yl)-3-[N-methyl-N-(2-(2,5-dimethyl-thienyl-3)-ethyl)-amino]-propane dihydrochloride The title compound is prepared analogously to Example 1 by reacting 1-(7,8-dimethoxy-1,3,4,5-tetrahydro-2H-3-benzazepin-2-on-3-yl)-3-chloro-propane with 2,5-dimethyl-3-(2-methylamino-ethyl)-thiophene and subsequently precipitating the dihydrochloride with ethereal hydrochloric acid.

Calculated: C 57.25, H 7.21, N 5.56, S 6.37, Cl 14.08, Found: 57.42, 7.44, 5.51, 6.76, 13.88.

$R_f$ value of the free base: 0.40 (silica gel, methylene chloride/methanol=10:1).

EXAMPLE 42

1-(7,8-Dimethoxy-1,3,4,5-tetrahydro-2H-3-benzazepin-2-on-3-yl)-3-[N-methyl-N-(3-(pyridyl-3-N-oxide)-propyl)-amino]-propane dihydrochloride hemihydrate Here, 1-(7,8-dimethoxy-1,3,4,5-tetrahydro-2H-3-benzazepin-2-on-3-yl)-3-N-methyl-amino-propane (2.9 g, 0.010 mol) and 3-(3-chloro-propyl)-pyridine-N-oxide (0.86 g, 0.005 mol) are reacted at 130° C. for 8 hours at a melt. The reaction product is dissolved in ethanol, purified over an aluminium oxide column with methylene chloride/methanol as eluant and the hydrochloride is precipitated with ethereal hydrochloric acid.

Yield: 0.40 g,

Melting point: 105°–115° C.

EXAMPLE 43

1-(7,8-Dimethoxy-1,3,4,5-tetrahydro-2H-3-benzazepin-1,2-dion-3-yl)-3-[N-methyl-N-(2-(pyridyl-4)-ethyl)amino]propane-dihydrochloride monohydrate The title compound is prepared analogously to Example 1 by reacting 1-(7,8-dimethoxy-1,3,4,5-tetrahydro-2H-3-benzazepin-1,2-dion-3-yl)-3-chloropropane with 4-(2-methylamino-ethyl)-pyridine and subsequently precipitating the hydrochloride with ethereal hydrochloric acid.

Melting point: 128°–132° C.

EXAMPLE 44

1-(7,8-Dimethoxy-1,3,4,5-tetrahydro-2H-3-benzazepin-2-on-3-yl)-3-[N-methyl-N-(2-(pyridyl-3-N-oxide)-ethyl)-amino]propane dihydrochloride hemihydrate Here, 3-(2-methylamino-ethyl)-pyridine-N-oxide (1.7 g, 0.011 mol) and 3-(7,8-dimethoxy-1,3,4,5-tetrahydro-2H-3-benzazepin-2-on-3-yl)-propionaldehyde (3.1 g, 0.011 mol) are dissolved in absolute ethanol (100 ml)

and molecular sieve 3 A (20 g) is added. After the addition of sodium borohydride (0.6 g, 0.016 mol) the mixture is stirred for 45 minutes at ambient temperature. It is suction filtered, decomposed with of 2N HCl (150 ml) and concentrated by evaporation. The residue is taken up with methylene chloride/conc. ammonia and the aqueous phase is extracted three times more with methylene chloride. The combined organic phases are dried, concentrated by evaporation, purified over a silica gel column and the dihydrochloride is precipitated with ethereal dihydrochloric acid.

Yield: 2.0 g,
Melting point: 216°–218° C.

EXAMPLE 45

1-(7,8-Dimethoxy-1,3,-dihydro-2H-3-benzazepin-2-on-3-yl)-3-[N-methyl-N-(2-(benzo[b]thienyl-3)-ethyl)-amino]-propane hydrochloride The title compound is prepared analogously to Example 31 by reacting 3-(7,8-dimethoxy-1,3,-dihydro-2H-3-benzazepin-2-on-3-yl)-propionaldehyde with 3-(2-methylamino-ethyl)-benzo[b]-thiophen and subsequently precipitating the dihydrochloride with ethereal hydrochloric acid.

$R_f$ value of the free base: 0.55 (silica gel, methylene chloride/methanol=9:1).

EXAMPLE 46

1-(7,8-Dimethoxy-1,3,4,5-tetrahydro-2H-3-benzazepin-2-on-3-yl)-3-[N-methyl-N-(2-(benzo[b]furyl-2)-ethyl)-amino]-propane-dihydrochloride The title compound is prepared analogously to Example 31 by reacting 3-(7,8-dimethoxy-1,3,4,5-tetrahydro-2H-3-benzazepin-2-on-3-yl)-propionaldehyde with 2-(2-methylamino-ethyl)-benzo-[b]furan and subsequently precipitating the dihydrochloride with ethereal hydrochlorid acid.

$R_f$ value of the free base: 0.42 (silica gel, methylene chloride/methanol=10.1).

EXAMPLE 47

1-(7,8-Dimethoxy-1,3,4,5-tetrahydro-2H-3-benzazepin-2,4-dion-3-yl)-3-[N-methyl-N-(2-(pyridyl-3)-ethyl)-amino]propane The title compound is prepared analogously to Example 31 by reacting 3-(7,8-dimethoxy-1,3,4,5-tetrahydro-2H-3-benzazepin-2,4-dion-3-yl)-propionaldehyde with 3-(2-methylamino-ethyl)-pyridine, but with hydrogenation being carried out at ambient temperature.

Melting point: 78°–80° Celsius

EXAMPLE 48

1-(7,8-Dimethoxy-1,3,4,5-tetrahydro-2H-3-benzazepin-2,4-dion-3-yl)-3-[N-methyl-N-(2-(6,7-dimethoxy-isoquinolyl-4)-ethyl)-amino]propane The title compound is prepared analogously to Example 31 by reacting 3-(7,8-dimethoxy-1,3,4,5-tetrahydro-2H-3-benzazepin-2,4-dion-3-yl)-propionaldehyde with 4-(2-methylamino-ethyl)-6,7-dimethoxy-isoquinoline, but with hydrogenation being carried out at ambient temperature.

$R_f$ value of the free base: 0.45 (silica gel, ethyl acetate/ethanol/ammonia=90:10:1).

EXAMPLE 49

1-(7,8-Dimethoxy-1,3,4,5-tetrahydro-2H-3-benzazepin-2-on-3-yl)-3-[N-methyl-N-((3,5-dimethyl-isoxazolyl-4)-methyl)-amino]-propane The title compound is prepared analogously to Example 2 by reacting 1-(7,8-dimethoxy-1,3,4,5-tetrahydro-2H-3-benzazepin-2-on-3-yl)-3-N-methyl-aminopropane with 4-chloromethyl-3,5-dimethyl-isoxazole.

Melting point: 93°–95° C.

EXAMPLE 50

1-(7,8-Dimethoxy-1,3,4,5-tetrahydro-2H-3-benzazepin-2-thion-3-yl)-3-[N-methyl-N-(2-(6-methoxy-benzo[b]-thienyl-3)-ethyl)-amino]propane The title compound is prepared analogously to Example 4 from 1-(7,8-dimethoxy-1,3,4,5-tetrahydro-2H-3-benzazepin-2-on-3-yl)-3-[N-methyl-N-(2-(6-methoxy-benzo[b]thienyl-3)-ethyl)-amino]propane and 2,4-Bis-(methylthio)-1,3-dithia-2,4-diphosphetan-2,4-disulfide.

$R_f$ value of the free base: 0.37 (silica gel, methylene chloride/methanol=9:1).

EXAMPLE 51

1-(7,8-Dimethoxy-1,3,4,5-tetrahydro-2H-3-benzazepin-2-on-3-yl)-3-[N-methyl-N-(2-(3-methyl-5-methoxy-benzo[b]furyl-2)-ethyl)-amino]propane The title compound is prepared analogously to Example 1 by reacting 1-(7,8-dimethoxy-1,3,4,5-tetrahydro-2H-3-benzazepin-2-on-3-yl)-3-chloro-propane with 2-(2-benzylamino-ethyl)-3-methyl-5-methoxybenzo[b]furan.

$R_f$ value of the free base: 0.65 (silica gel, methylene chloride/methanol=9:1).

EXAMPLE 52

1-(7,8-Dimethoxy-1,3,4,5-tetrahydro-2H-3-benzazepin-2-on-3-yl)-3-[N-((thienyl-2)-methyl)-amino]propane The title compound is prepared analogously to Example 1 by reacting 1-(7,8-dimethoxy-1,3,4,5-tetrahydro-2H-3-benzazepin-2-on-3-yl)-3-chloro-propane with 2-aminomethyl-thiophene.

Calculated: C 64.14, H 7.00, N 7.48, S 8.56, Found: C 63.90, H 7.06, N 7.41 S 8.81.

$R_f$ value of the free base: 0.32 (silica gel, methylene chloride/methanol=9:1).

EXAMPLE 53

1-(7,8-Dimethoxy-1,3,4,5-tetrahydro-2H-3-benzazepin-2-on-3-yl)-3-[N-methyl-N-(2-(4-methoxy-benzo[b]furyl-3)-ethyl)-amino]propane The title compound is prepared analogously to Example 1 by reacting 1-(7,8-dimethoxy-1,3,4,5-tetrahydro-2H-3-benzazepin-2-on-3-yl)-3-chloro-propane with 3-(2-methylamino-ethyl)-4-methoxy-benzo[b]furan.

$R_f$ value of free base: 0.21 (silica gel, methylene chloride/methanol=9:1).

EXAMPLE 54

1-(7,8-Dimethoxy-1,3,4,5-tetrahydro-2H-3-benzazepin-2-on-3-yl)-3-[N-methyl-N-(2-(4,5,6,7-tetrahydro-benzo[b]thienyl-3)-ethyl)-amino]propane The title compound is prepared analogously to Example 1 by reacting 1-(7,8-dimethoxy-1,3,4,5-tetrahydro-2H-3-benzazepin-2-on-3-yl)-3-chloro-propane with 3-(2-methylamino-ethyl)-4,5,6,7-tetrahydrobenzo[b]thiophene.

R$_f$ value of the free base: 0.40 (silica gel, methylene chloride/methanol=10:1).

EXAMPLE 55

1-(7,8-Dimethoxy-1,3,4,5-tetrahydro-2H-3-benzazepin-2-on-3-yl)-3-[N-methyl-N-(2-(6-hydroxy-benzo[b]thienyl-3)-ethyl)-amino]propane The title compound is prepared analogously to Example 1 by reacting 1-(7,8-dimethoxy-1,3,4,5-tetrahydro-2H-3-benzazepin-2-on-3-yl)-3-(N-methyl-amino)-propane with 3-(2-chloro-ethyl)-6-hydroxy-benzo[b]thiophene.

R$_f$ value of the free base: 0.45 (aluminum oxide methylene chloride/methanol=10:1).

EXAMPLE 56

1-(7,8-Dimethoxy-1,3,4,5-tetrahydro-2H-3-benzazepin-2-on-3-yl)-3-[N-methyl-N-(2-(6-methylsulphonyloxy-benzo[b]thienyl-3)-ethyl)-amino]propane The title compound is prepared analogously to Example 1 by reacting 1-(7,8-dimethoxy-1,3,4,5-tetrahydro-2H-3-benzazepin-2-on-3-yl)-3-(N-methyl-amino)-propane with 3-(2-chloro-ethyl)-6-methylsulphonyloxy-benzo[b]thiophene.

R$_f$ value of the free base: 0.49 (silica gel, methylene chloride/methanol=9:1).

EXAMPLE 57

1-(7,8-Dimethoxy-1,3,4,5-tetrahydro-2H-3-benzazepin-2-on-3-yl)-3-[N-methyl-N-(2-(benzo[b]thienyl-4)-ethyl)-amino]propane-dihydrochloride The title compound is prepared analogously to Example 1 by reacting 1-(7,8-dimethoxy-1,3,4,5-tetrahydro-2H-3-benzazepin-2-on-3-yl)-3-chloro-propane with 4-(2-methylamino-ethyl)-benzo[b]thiophene and subsequently precipitating the dihydrochloride with ethereal hydrochloric acid.

Melting point: 198° C. (decomp.)

Calculated: C 59.42, H 6.52, N 5.33, Cl 13.49, S 6.10, Found: C 59.26, H 6.58, N 5.39, Cl 13.28, S 6.51.

EXAMPLE I

Tablets containing 10 mg of 1-(7,8-dimethoxy-1,3,4,5-tetrahydro-2H-3-benzazepin-2-on-3-yl)-3-[N-methyl-N-(2-(benzo[b]thienyl-3)-ethyl)-amino]propane-hydrochloride Composition:

| 1 tablet contains: | |
|---|---|
| Active substance | 10.0 mg |
| Corn starch | 57.0 mg |
| Lactose | 48.0 mg |
| Polyvinylpyrrolidone | 4.0 mg |
| Magnesium stearate | 1.0 mg |
| | 120.0 mg |

Method of preparation

The active substance, corn starch, lactose and polyvinylpyrrolidone are mixed together and moistened with water. The moist mixture is pushed through a screen with a mesh size of 1.5 mm and dried at about 45° C. The dry granulate is passed through a 1.0 mm mesh screen and mixed with magnesium stearate. The final mixture is compressed in a tablet press with dies 7 mm in diameter provided with a dividing notch to form tablets.

Weight of tablet: 120 mg.

EXAMPLE II

Coated tablets containing 5 mg of 1-(7,8-dimethoxy-1,3,4,5-tetrahydro-2H-3-benzazepin-2-on-3-yl)-3-[N-methyl-N-(2-(benzo[b]thienyl-3)-ethyl)-amino]propanehydrochloride

| 1 tablet core contains: | |
|---|---|
| Active substance | 5.0 mg |
| Corn starch | 41.5 mg |
| Lactose | 30.0 mg |
| Polyvinylpyrrolidone | 3.0 mg |
| Magnesium stearate | 0.5 mg |
| | 80.0 mg |

Method of Preparation

The active substance, corn strach, lactose and polyvinylpyrrolidone are throughly mixed and moistened with water. The moist mass is forced through a 1 mm screen, dried at about 45° C. and then the granulate is passed through the same screen. After magnesium stearate has been added, convex tablet cores with a diameter of 6 mm are compressed in a tablet making machine. The table cores thus produced are coated in known manner with a coating consisting essentially of sugar and talc. The finished coated tablets are polished with wax.

Weight of coated tablet: 130 mg.

EXAMPLE III

Ampoules containing 5 mg of 1-(7,8-dimethoxy-1,3,4,5-tetrahydro-2H-3-benzazepin-2-on-3-yl)-3-[N-methyl-N-(2-(benzo[b]thienyl-3)-ethyl)-amino]propane-hydrochloride

| 1 ampoule contains: | |
|---|---|
| Active substance | 5.0 mg |
| Sorbitol | 50.0 mg |
| Water for injections ad. | 2.0 ml |

Method of Preparation

In a suitable mixing vessel the active substance is dissolved in water for injections and the solution is made isotonic with sorbitol. After being filtered through a diaphragm filter the solution is transfered under a current of N$_2$ into purified and sterilized ampoules and autoclaved for 20 minutes in a jet of steam.

EXAMPLE IV

Suppositories containing 15 mg of 1-(7,8-dimethoxy-1,3,4,5-tetrahydro-2H-3-benzazepin-2-on-3-yl)-3-[N-methyl-N-(2-(benzo[b]thienyl-3)-ethyl)-amino]propanehydrochloride

| 1 suppository contains: | |
|---|---|
| active substance | 0.015 g |
| Hard fat (e.g. Witepsol H 19 and W 45) | 1.685 g |
| | 1.700 g |

Method of Preparation

The hard fat is melted. At 38° C. the ground active substance is homogeneously dispersed in the melt. It is cooled to 35° C. and poured into slightly chilled suppository moulds.

EXAMPLE IV

Drops solution containing 10 mg of 1-(7,8-dimethoxy-1,3,4,5-tetrahydro-2H-3-benzazepin-2-on-3-yl)-3-[N-methyl-N-(2-(benzo[b]thienyl-3)-ethyl)-amino]propanehydrochloride

| 100 ml of solution contain: | |
| --- | --- |
| Active substance | 0.2 g |
| Hydroxyethylcellulose | 0.15 g |
| Tartaric acid | 0.1 g |
| Sorbitol solution with 70% dry matter | 30.0 g |
| Glycerol | 10.0 g |
| Benzoic acid | 0.15 g |
| Dist. water ad | 100 ml |

Method of Preparation

The distilled water is heated to 70° C. The hydroxyethylcellulose, benzoic acid and tartaric acid are dissolved therein with stirring. The mixture is cooled to ambient temperature and the glycerol and sorbitol solution are added with stirring. At ambient temperature the active substance is added and stirred until completely dissolved. The syrup is then evacuated of any air with stirring.

What is claimed is:

1. A compound of formula I:

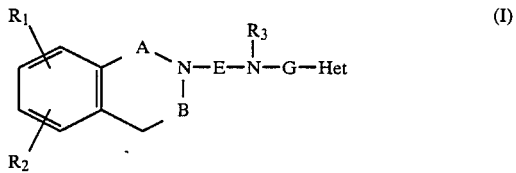

wherein
A represents a —CH$_2$—CH$_2$—, —CH=CH— or

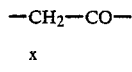

group and B represents a methylene, carbonyl or thiocarbonyl group or
A represents a —CO—CO or

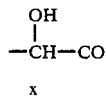

group and B represents a methylene group,
in which the carbon atom marked x is linked to the phenyl nucleus,
E represents a straight-chained alkylene group having 2 to 4 carbon atoms optionally substituted by an alkyl group having 1 to 3 carbon atoms,
G represents a straight-chained alkylene group having 1 to 5 carbon atoms optionally substituted by an alkyl group having 1 to 3 carbon atoms,
R$_1$ represents a hydrogen, fluorine, chlorine or brmine atom, a trifluoromethyl, nitro, amino, alkylamino, dialkylamino, alkyl, alkylmercapto, hydroxy, alkoxy or phenylalkoxy group, in which each alkyl part can contain from 1 to 3 carbon atoms,
R$_2$ represents a hydrogen, chlorine or bromine atom or a hydroxy, alkoxy, phenylalkoxy or alkyl group, in which each alkyl part can contain from 1 to 3 carbon atoms, or
R$_1$ and R$_2$ together represent an alkylenedioxy group having 1 or 2 carbon atoms,
R$_3$ represents a hydrogen atom, an alkenyl group having 3 to 5 carbon atoms, an alkyl or phenylalkyl group, in which the alkyl part can contain 1 to 3 carbon atoms, and
Het can represent a pyrrolyl-2-, pyrrolyl-3-, N-methyl-pyrrolyl-2-, N-methyl-pyrrolyl-3-, 1,2-dimethyl-pyrrolyl-3-, 2,5-dimethyl-pyrrolyl-3-, furyl-2-, furyl-3-, 5-methyl-furyl-2-, 2-methyl-furyl-3-, 5-nitro-furyl-2-, 5-methoxymethyl-furyl-2-, benzo[b]furyl-2-, benzo[b]furyl-3-, 7-methyl-benzo[b]furyl-3-, 2-methoxy-benzo[b]furyl-3-, 3-methoxy-benzo[b]furyl-2-, 4-methoxy-benzo[b]furyl-3, 5-methoxy-benzo[b]furyl-3-, 6-methoxy-benzo[b]furyl-3-, 7-methoxy-benzo[b]furyl-3-, 5-methoxy-3-phenyl-benzo[b]furyl-2-, 3-methyl-5-methoxy-benzo[b]furyl-2-, thienyl-2-, thienyl-3-, 5-methyl-thienyl-2-, 2-methyl-thienyl-3-, 3-methyl-thienyl-2-, 2,5-dimethyl-thienyl-3-, 4,5,6,7-tetrahydro-benzo[b]thienyl-2-, 4,5,6,7-tetrahydro-benzo[b]thienyl-3-, 5-chloro-thienyl-2-, 5-bromo-thienyl-2-, 5-phenyl-thienyl-2-, 2-phenyl-thienyl-3-, benzo[b]thienyl-2-, benzo[b]thienyl-3-, 2,5-dimethyl-benzo[b]thienyl-3-, 5-methyl-benzo[b]thienyl-3-, 6-methyl-benzo[b]thienyl-3-, 5-chloro-benzo[b]-thienyl-2-, 5-bromo-benzo[b]thienyl-3-, 6-hydroxy-benzo[b]thienyl-3, 7-hydroxy[b]thienyl-3-, 5-hydroxy-benzo[b]thienyl-2-, 6-hydroxy-benzo[b]-thienyl-2-, 7-hydroxy-benzo[b]thienyl-2-, 3-methoxy-benzo[b]thienyl-2-, 4-methoxy-benzo[b]thienyl-2-, 5-methoxy-benzo[b]thienyl-2-, 6-methoxyl-benzo[b]thienyl-2-, 7-methoxy-benzo[b]thienyl-2-, 2-methoxy-benzo[b]thienyl-3-, benzo[b]thienyl-4-, benzo[b]thienyl-5-, benzo[b]thienyl-6-, benzo[b]thienyl-7-, 4-methoxy-benzo[b]thienyl-3-, 5-methoxy-benzo[b]thienyl-3-, 6-methoxy-benzo[b]thienyl-3-, 7-methoxy-benzo[b]thienyl-3-, 5,6-dimethoxy-benzo[b]thienyl-3-, 5,6-methylenedioxy-benzo[b]thienyl-3-, 6-ethoxy-benzo[b]thienyl-3-, 6-propoxy-benzo[b]thienyl-3-, 6-isopropoxybenzo[b]thienyl-3-, 6-mercapto-benzo[b]thienyl-3-, 6-methylmercapto-benzo[b]thienyl-3-, 6-methylsulfinyl-benzo[b]thienyl-3-, 6-methyl-sulfonyl-benzo[b]thienyl-3-, 6-methylsulfonyloxy-benzo[b]thienyl-3-, 6-methoxycarbonylmethoxy-benzo[b]thienyl-3-, 6-ethoxycarbonylmethoxy-benzo[b]thienyl-3-, 6-carboxymethoxy-benzo[b]thienyl-3-, 6-amino-benzo[b]thienyl-3-, 6-methylamino-benzo[b]thienyl-3-, 6-dimethylamino-benzo-[b]thienyl-3-, 6-diethylaminobenzo[b]thienyl-3-, 6-acetamino-benzo[b]thienyl-3-, 6-methylsulfonylamino-benzo[b]thienyl-3-, pyrazolyl-1-, pyrazolyl-3-, 3,5-dimethyl-pyrazolyl-1-, 1,5-dimethyl-pyrazolyl-3-, imidazolyl-1-, imidazolyl-2-, imidazolyl-4(5), 1-methyl-imidazolyl-4-, 1-benzyl-imidazolyl-4-, 5-nitro-2-methyl-imidazolyl-1-, 2-(3,4-dimethoxyphenyl)-imidazolyl-4(5)-, benzo[d]imidazolyl-1,2-benzyl-benzo[d]imidazolyl-1-, benzo[d]imidazolyl-2-, imidazo[1,2-a]pyridyl-3-,oxazolyl-4-, oxazolyl-5-, isoxazolyl-3-, 3-methyl-isoxazolyl-5-, 5-methyl-isoxazolyl-3-, 3,5-dimethyl-isoxazolyl-4-, 4-methyl-thiazolyl-5-, benzo[d]oxazolyl-2-, benzo[d]isoxazolyl-3-, benzo[d]thiazolyl-2-, 5-ethoxy-benzo[d]thiazoly-2-, benzo[d]isothiazolyl-3-, benzo[d-

]pyrazolyl-1-, benzo[d]pyrazolyl-3-, pyridyl-2-, pyridyl-3, pyridyl-4-, pyridyl-3-N-oxide-, 4-nitro-pyridyl-2-, 4-amino-pyridyl-2-, 4-acetylamino-pyridyl-2,4-carbamoylamino-pyridyl-2-, 4-N-methyl-carbamoylamino-pyridyl-2-, 2-chloro-pyridyl-3-, 2-chloro-pyridyl-4-, 6-chloro-pyridyl-2-, 6-hydroxymethylpyridyl-2-, quinolyl-2-, isoquinolyl-1-, 2-methylquinolyl-4-, 7-methyl-quinolyl-2-, 4-chloro-quinolyl-2-, 6,7-dimethoxy-quinolyl-4-, 6,7-dimethoxy-isoquinolyl-4- or 6,7-dimethoxy-isoquinolyl-4-N-oxide group
and the nontoxic, pharmaceutically acceptable acid addition salts thereof.

2. A compound of formula Ia:

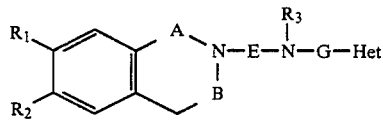

wherein
A represents a —CH$_2$—CH$_2$—, —CH=CH—,

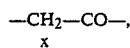

—CO—CO— or

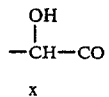

group and B represents a methylene group or
A represents a —CH$_2$—CH$_2$— or —CH=CH— group and B represents a carbonyl or thiocarbonyl group, in which the carbon atom designated x is in each case linked to the phenyl nucleus,
E represents an n-propylene group,
G represents an ethylene, n-propylene or n-butylene group,
R$_1$ represents a chlorine or bromine atom or a methyl, methoxy, nitro, amino, methylamino or dimethylamino group,
R$_2$ represents a chlorine or bromine atom or a methyl or methoxy group or R$_1$ and R$_2$ together represent a methylenedioxy or ethylenedioxy group,
R$_3$ represents a hydrogen atom or a methyl, ethyl or allyl group and
Het represents a pyrrolyl-2-, pyrrolyl-3-, N-methyl-pyrrolyl-2-, N-methyl-pyrrolyl-3-, furyl-2-, benzo[b]furyl-2-, benzo[b]furyl-3-, 7-methyl-benzo[b]furyl-3-, 6-methoxy-benzo[b]furyl-3-, 5-methoxy-3-phenyl-benzo[b]furyl-2-, thienyl-2-, thienyl-3-, 5-methylthienyl-2-, 2,5-dimethyl-thienyl-3-, 5-bromo-thienyl-2-, benzo[b]thienyl-2-, benzo[b]thienyl-3-, 6-hydroxybenzo[b]thienyl-3-, 6-methoxy-benzo[b]thienyl-3-, 5,6-dimethoxy-benzo[b]thienyl-3-, 2,5-dimethyl-benzo[b]thienyl-3-, 5-methoxy-benzo[b]thienyl-2-, 6-methoxy-benzo[b]thienyl-2-, 6-methylmercapto-benzo[b]thienyl-3-, 6-methylsulfinyl-benzo[b]thienyl-3-, 6-methylsulfonyl-benzo[b] thienyl-3-, 6-methylsulfonyloxy-benzo[b]thienyl-3-, 6-ethoxycarbonylmethoxy-benzo[b]thienyl-3-, 6-carboxymethoxy-benzo[b]thienyl-3-, 6-dimethylamino-benzo[b]thienyl-3-, 6-methylsulfonylamino-benzo[b]thienyl-3-, 6-acetamino-benzo[b]-thienyl-3-, benzo[b]thienyl-4-, pyrazolyl-1-, pyrazolyl-3-, 1,5-dimethyl-pyrazolyl-3-, 1-methyl-imidazolyl-4-, 2-(3,4-dimethoxy-phenyl)-imidazolyl-4(5)-, benzo[d]imidazolyl-1-, 2-benzyl-benzo[d]imidazolyl-1-, imidazol[1,2-a]pyridyl-3-, oxazolyl-4-, oxazolyl-5-, isoxazolyl-3-, 3-methyl-isoxazolyl-5-, 4-methylthiazolyl-5-, pyridyl-2-, pyridyl-3-, pyridyl-4-, pyridyl-3-N-oxide, 4-nitro-pyridyl-2-, 4-amino-pyridyl-2-, 4-acetylamino-pyridyl-2-, 4-carbamoylamino-pyridyl-2-, 4-N-methyl-carbamoylamino-pyridyl-2-, 6,7-dimethoxy-quinolyl-4-, 6,7-dimethoxy isoquinolyl-4-, or 6,7-dimethoxy-isoquinolyl-4-N-oxide group, and the nontoxic, pharmaceutically acceptable acid addition salts thereof.

3. A compound of claim 2 wherein
A represents a —CH$_2$—CH$_2$— or —CH=CH— group and B represents a carbonyl or thiocarbonyl group,
E represents an n-propylene group,
G represents an ethylene, n-propylene or n-butylene group,
R$_1$ and R$_2$ each represent a methoxy group or R$_1$ and R$_2$ together represent a methylenedioxy group,
R$_3$ represents a hydrogen atom or a methyl group and
Het represents a pyrrolyl-2-, pyrrolyl-3-, N-methylpyrrolyl-2-, N-methyl-pyrrolyl-3-, thienyl-2-, thienyl-3-, 5-methyl-thienyl-2-, 2,5-dimethyl-thienyl-3-, 5-bromo-thienyl-2-, pyrazolyl-1-, pyrazolyl-3-, 1-methyl-imidazolyl-4-, isoxazolyl-3-, benzo[b]furyl-2-, benzo[b]furyl-3-, 7-methyl-benzo[b]furyl-3-, 6-methoxybenzo[b]furyl-3-, 7-methoxy-benzo[b]furyl-3-, benzo[b]thienyl-2-, benzo[b]thienyl-3-, 6-methoxybenzo[b]thienyl-3-, 6-methylsulfonyloxy-benzo[b]thienyl-3-, 6-ethoxycarbonylmethoxy-benzo[b]thienyl-3-, 6-carboxymethoxy-benzo[b]thienyl-3-, 6-acetamino-benzo[b]thienyl-3-, benzo[d]imidazolyl-1-, imidazo[1,2-a]pyridyl-3- or pyridyl group, and the non-toxic, pharmaceutically acceptable acid addition salts thereof.

4. 1-(7,8-Dimethoxy-1,3,4,5-tetrahydro-2H-3-benzazepin-2-on-3-yl)-3-[N-methyl-N-(2-(6-methoxybenzo[b]thienyl-3)-ethyl)-amino]propane and the nontoxic, pharmaceutically acceptable acid addition salts thereof.

5. 1-(7,8-Dimethoxy-1,3,4,5-tetrahydro-2H-3-benzazepin-2-on-3-yl)-3-[N-methyl-N-(2-(6-methoxybenzo[b]furyl-3)-ethyl)-amino]propane and the nontoxic, pharmaceutically acceptable acid addition salts thereof.

6. 1-(7,8-Dimethoxy-1,3,4,5-tetrahydro-2H-3-benzazepin-2-on-3-yl)-3-[N-methyl-N-(2-(benzo[b]furyl-2)-ethyl)-amino]propane and the nontoxic, pharmaceutically acceptable acid addition salts thereof.

7. 1-(7,8-Dimethoxy-1,3,4,5-tetrahydro-2H-3-benzazepin-2-on-3-yl)-3-[N-methyl-N-(2-(benzo[b]thienyl-3)-ethyl)amino]propane and the nontoxic, pharmaceutically acceptable acid addition salts thereof.

8. 1-(7,8-Dimethoxy-1,3,4,5-tetrahydro-2H-3-benzazepin-2-on-3-yl)-3-[N-methyl-N-(4-(thienyl-2)-butyl)amino]propane and the nontoxic, pharmaceutically acceptable acid addition salts thereof.

9. A pharmaceutical composition for lowering heart rate or oxygen requirement of the heart or for treating sinus tachycardia or ischaemic heart disease, which composition comprises a therapeutically effective amount of a compound of any of claims 1 to 3 and at least one inert carrier and/or diluent.

10. A method of lowering the heart rate or oxygen consumption of the heart in an individual in need thereof which comprises administering to said individual an amount of a compound of any of claims 1 to 3 which is effective to lower the heart rate or heart oxygen consumption in said individual.

11. A method of treating sinus tachycardia or ischaemic heart disease in an individual in need thereof which comprises administering to said individual a therapeutically effective amount of a compound of any of claims 1 to 3.

* * * * *